United States Patent
Wu et al.

(10) Patent No.: US 10,784,000 B2
(45) Date of Patent: Sep. 22, 2020

(54) MEDICAL SYSTEM INTERFACE APPARATUS AND METHODS TO CLASSIFY AND PROVIDE MEDICAL DATA USING ARTIFICIAL INTELLIGENCE

(71) Applicant: VVC Holding Corporation, Seattle, WA (US)

(72) Inventors: Eric Wu, Mukilteo, WA (US); Wei Huang, Bellevue, WA (US)

(73) Assignee: VVC HOLDING CORPORATION, Watertown, MA (US)

( * ) Notice: Subject to any disclaimer, the term of this patent is extended or adjusted under 35 U.S.C. 154(b) by 173 days.

(21) Appl. No.: 16/136,984

(22) Filed: Sep. 20, 2018

(65) Prior Publication Data

US 2019/0287684 A1   Sep. 19, 2019

Related U.S. Application Data

(60) Provisional application No. 62/644,117, filed on Mar. 16, 2018.

(51) Int. Cl.
  *G16H 10/00*  (2018.01)
  *G16H 50/70*  (2018.01)
  (Continued)

(52) U.S. Cl.
  CPC .......... *G16H 50/70* (2018.01); *G06F 40/284* (2020.01); *G06F 40/295* (2020.01);
  (Continued)

(58) Field of Classification Search
  CPC ........ G16H 10/00; G16H 10/60; G06F 19/32; G06F 40/284
  See application file for complete search history.

(56) References Cited

U.S. PATENT DOCUMENTS 6,915,254 B1   7/2005   Heinze et al.
7,610,192 B1   10/2009  Jamieson
(Continued)

*Primary Examiner* — Daniel Abebe
(74) *Attorney, Agent, or Firm* — GTC Law Group PC & Affiliates

(57) ABSTRACT

Apparatus, systems, devices, other articles of manufacture and associated methods are disclosed and described herein to process medical data to generate a classification of the medical data using artificial intelligence. An example apparatus includes a processor to execute instructions to implement a history of past illness (HPI) receiver to receive an HPI formatted as a string, the string including one or more words, the words organized in sentences, a natural language processor to tokenize the one or more words into tokens based on a context associated with at least one of the one or more words and a tensor generator to convert the tokens into hashes, each of the hashes forming a dimension of a tensor based on the context. The apparatus further includes a neural network to embed each of the hashes into vectors, process the vectors to classify the HPI as extended or brief based on a similarity to a set of classified HPIs and output a classification for the HPI. The apparatus further includes an electronic medical record modifier to modify an electronic medical record with the HPI and the classification and to trigger an action with respect to the electronic medical record based on the classification.

20 Claims, 11 Drawing Sheets

(51) Int. Cl.
  *G06N 3/04*      (2006.01)
  *G16H 10/60*     (2018.01)
  *G16H 50/20*     (2018.01)
  *G06K 9/62*      (2006.01)
  *G06F 40/284*    (2020.01)
  *G06F 40/295*    (2020.01)

(52) U.S. Cl.
  CPC ......... *G06K 9/6279* (2013.01); *G06N 3/0481* (2013.01); *G16H 10/60* (2018.01); *G16H 50/20* (2018.01)

(56) References Cited

U.S. PATENT DOCUMENTS

| | | |
|---|---|---|
| 8,260,779 B2 | 9/2012 | Hudgins et al. |
| 8,346,804 B2 | 1/2013 | Phillips |
| 8,639,522 B2 | 1/2014 | Pathria et al. |
| 2011/0066425 A1* | 3/2011 | Hudgins ................ G06Q 10/10 704/10 |
| 2013/0124523 A1* | 5/2013 | Rogers ................... G16H 10/60 707/737 |
| 2014/0095205 A1 | 4/2014 | Farooq et al. |
| 2016/0019356 A1 | 1/2016 | Martin et al. |
| 2016/0048655 A1* | 2/2016 | Maitra ................... G16H 10/60 705/3 |
| 2017/0228500 A1* | 8/2017 | Massengale ........... G16H 10/60 |
| 2019/0005019 A1* | 1/2019 | Burke .................... G06F 19/36 |
| 2019/0208354 A1* | 7/2019 | Raduchel ............. H04W 12/06 |

\* cited by examiner

MEDICAL SYSTEM INTERFACE APPARATUS AND METHODS TO CLASSIFY AND PROVIDE MEDICAL DATA USING ARTIFICIAL INTELLIGENCE

RELATED APPLICATION

This patent arises from U.S. Provisional Patent Application Ser. No. 62/644,117, which was filed on Mar. 16, 2018. U.S. Patent Application Ser. No. 62/644,117 is hereby incorporated herein by reference in its entirety. Priority to U.S. Patent Application Ser. No. 62/644,117 is hereby claimed.

FIELD OF THE DISCLOSURE

This disclosure relates generally to managing electronic medical records and, more particularly, to methods and apparatus to classify medical data using artificial intelligence.

BACKGROUND

A patient's electronic medical records (EMR) are documentation of that patient's history of care and medical encounters stored in an electronic database. During a medical encounter, a healthcare professional usually takes a medical history of that patient. Aspects of a taking a medical history include asking questions to obtain a demographic information, chief complaint (CC), a history of the present illness (HPI), a review of systems (ROS) and past, family and/or social history (PFSH). The Center of Medicare and Medicaid (CMS) divides medical histories into four types, namely: problem focused, focus expanded problem, detailed and comprehensive. An amount of money reimbursed to a healthcare provider often depends on what type of medical history was taken during a medical encounter. A classification of medical history into these four types depends on information included in the gathered HPI, ROS and/or PFSH. CMS standards for medical history include:

TABLE 1

CMS Standards for Medical History

| Type of History | HPI | ROS | PFSH |
| --- | --- | --- | --- |
| Problem Focused | Brief | N/A | N/A |
| Focused Expanded Problem | Brief | N/A | N/A |
| Detailed | Extended | Pertinent | Pertinent |
| Comprehensive | Extended | Complete | Complete |

HPIs are narrative summaries compiled by a healthcare professional after identifying a patient's chief compliant (e.g., a reason for their visit). Classifying an HPI as "brief" or "extended" depends upon what information is obtained from the patient and recorded during the interview. The CMS has established a criterion such that an HPI is classified as "extended" when it contains four or more of the following elements: (1) location of problem, (2) quality of problem, (3) severity of problem, (4) duration of problem, (5) context of problem, (6) modifying factors, and (7) associated signs and symptoms. An HPI is classified as "brief" when it contains three or fewer elements. Historically, HPIs are classified by healthcare professionals during or after they are obtained or recorded.

SUMMARY

An example apparatus includes a processor to execute instructions to implement at least: a history of past illness (HPI) receiver to receive an HPI formatted as a string, the string including one or more words, the words organized in an order of sentences; a natural language processor to tokenize the one or more words into tokens based on a context associated with at least one of the one or more words; a tensor generator to convert the tokens into hashes, each of the hashes forming a dimension of a tensor based on the context; a neural network to: embed each of the hashes into vectors; process the vectors to classify the HPI as extended or brief based on a similarity to a set of classified HPIs; and output a classification for the HPI; and a medical system interface to modify a medical support system with the HPI and the classification and to trigger an action with respect to the medical support system based on the classification.

An example method includes receiving an HPI formatted as a string, the string including one or more words, the words organized in an order of sentences; tokenizing the one or more words into tokens based on a context associated with at least one of the one or more words; converting the tokens into hashes, each of the hashes forming a dimension of a tensor based on the context; embedding each of the hashes into vectors; processing the vectors to classify the HPI as extended or brief based on a similarity to a set of classified HPIs; and outputting a classification for the HPI; and modifying a medical support system with the HPI and the classification and to trigger an action with respect to the medical support system based on the classification.

An example tangible machine readable medium comprising instructions, which when executed, cause a processor to at least receive an HPI formatted as a string, the string including one or more words, the words organized in an order of sentences; tokenize the one or more words into tokens based on a context associated with at least one of the one or more words; convert the tokens into hashes, each of the hashes forming a dimension of a tensor based on the context; embed each of the hashes into vectors; process the vectors to classify the HPI as extended or brief based on a similarity to a set of classified HPIs; and output a classification for the HPI; and modify a medical support system with the HPI and the classification and to trigger an action with respect to the medical support system based on the classification.

BRIEF DESCRIPTION OF THE FIGURES

The features and technical aspects of the system and method disclosed herein will become apparent in the following Detailed Description in conjunction with the drawings in which reference numerals indicate identical or functionally similar elements.

DETAILED DESCRIPTION

Figure 1:
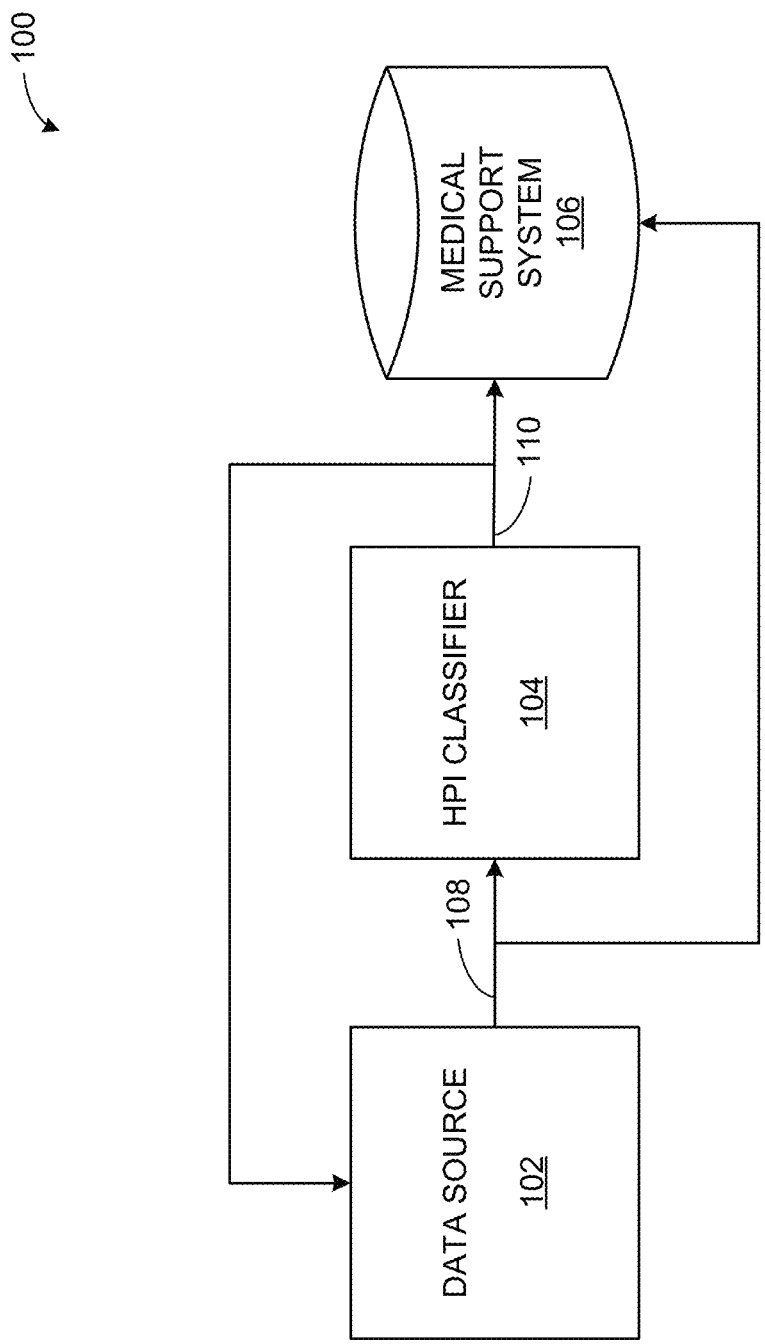
FIG. 1 is an illustration of a medical data processing system in which the teachings of this disclosure may be implemented.

In the following detailed description, reference is made to the accompanying drawings that form a part hereof, and in which is shown by way of illustration specific examples that may be practiced. These examples are described in sufficient detail to enable one skilled in the art to practice the subject matter, and it is to be understood that other examples may be utilized and that logical, mechanical, electrical and other changes may be made without departing from the scope of the subject matter of this disclosure. The following detailed description is, therefore, provided to describe an exemplary implementation and not to be taken as limiting on the scope of the subject matter described in this disclosure. Certain features from different aspects of the following description may be combined to form yet new aspects of the subject matter discussed below.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements.

Acquisition, analysis, classification and storage of information gathered while taking a medical history is important to the diagnosis and treatment of patient. Additionally, reimbursements from organizations like the CMS often depend on the quality of information gathered during while taking medical history. For example, generally more detailed medical histories (e.g., detailed or comprehensive histories, see table 1) garner high reimbursement fees from CMS. One determining factor in deciding if a medical history is detailed or comprehensive is determining if the taken HPI is "extended" or "brief." Historically, when an HPI is taken from a patient and recorded in the EMR of the patient, a healthcare professional would classify the HPI based the presence of seven elements.

As computers continue to take on a greater role in patient care, automating the process for determining if an HPI is "extended" or "brief" becomes important to the maintenance and completeness of an EMR of a patient. Automating the process of classifying an HPI potentially allows an HPI to be gathered by a computer instead of a healthcare professional, thus allowing healthcare professionals to be performing more critical tasks. Additionally, empirical evidence suggests humans incorrectly classify HPIs at a relatively high and significant rate. Automating the classification process could potentially alleviate some of these potential issues. In some examples, this may lead to more accurate medical records for the patient and more accurate billing for the CMS and healthcare organizations. Furthermore, automatic classification of an HPI as "brief," may encourage a healthcare professional to retake an HPI to ensure the HPI is "extended."

However, HPIs resist being easily classified by standard artificial intelligences (AI) and/or natural language processors (NLPs) for a number of reasons. First, HPIs are often recorded as a narrative which makes identifying which, if any, of the seven elements are present in a particular patient's HPI difficult. Because each HPI is recorded by a different healthcare professional, the writing style (e.g., punctuation, abbreviations, word choice, sentence structure, etc.) of each narrative can vary. Additionally, in some examples, the narrative may contain misspelled words or incomplete sentences. Second, the HPIs often contain high occurrences of medical terms, abbreviations and named entities which often have different meanings depending on the context. For example, "pt" can refer to either "patient" or "physical therapy" depending on the context. Abbreviations such as "OSA" (obstructive sleep apnea), "PSA" (prostate specific antigen), etc., can be difficult to process. Similarly, named entities such as "Dr. Smith", "CPCA (California Primary Care Association)", etc., can also be difficult to process. Third, HPIs often contain extensive use of numbers with different semantic meanings. For examples, the phrases "last colonoscopy was 2009," "the pain lasts 5 minutes," and "Type 2 Diabetes" all contain numbers with different semantic meanings (e.g., a date, a duration and a classification of disease, respectively). Fourth, the length (e.g., word count, number of sentences, etc.) of an HPI does not necessarily correlate with its classification.

For example, the following HPI is relatively long but would be classified as a brief HPI:

> The patient comes in today for annual GYN exam. The patient has no history of no GYN complaints, abnormal period, pelvic pain, abnormal vaginal discharge, breast mass, breast pain, depression, anxiety, urinary symptoms, chest pain, palpations, shortness of breath, leg swelling, back pain, abdominal pain, headaches, bowel problems, menopausal issues, PMS, amenorrhea, and dysmenorrhea. Patient is a 58 YEARS Old G1P1 who presents for an annual exam. Last exam was 2009 with Kaiser. Hysterectomy 2003 (supracerivcal). Mild hot flashes, when emotional stress is high. Pt needs mammogram. PT is taking calcium+D. Pt has colonoscopy 2007, polyps removed. I recommend that pt see PCP for referral to GI. Pt mentions urinary frequency. She attributes this to diuretic. No urgency. No dysuria. Pt gets regular exercise.

This HPI contains two elements, context (e.g., "mild hot flashes when emotional stress is high") and modifying factors ("attributes hot flashes to diuretic") and is therefore considered a "brief" HPI, rather than an "extended" HPI. Another example of an HPI that is likely to be identified as an "extended" HPI but is in fact brief because it only focuses on past medical history rather than the present illness is as follows (including typos):

> xxx is a 21 month old boy who presents for initial pulmonary consult. The patient comes in today with his mother for evaluation of recurrent cough and wheezing. Mother reports that xxx was seen in the ER twice last year for an episode of increased coughing, wheezing and increased work fo breathing. He had a chest xray done once which did not reveal any pneumonia. He was placed on Albuterol nebs and oral steroids with improvement of the symptoms. Since then, mother reports that xxx has developed episodes of coughing and wheezing with viral URI. He had a several respiratory flare ups in the last 3 months. The most recent was 2 weeks ago. He presented with increased coughing and increased heart rate. He was brought to the ER and was advised to take the Albuterol and not need to be on the oral steroids. During this visit, mother reports that xxx has been doing better. He still has intermittent coughing but decreased in frequency. He has been taking the Pulmicort nebs twice a day in the last 2 weeks and also receiving the Albuterol nebs twice a day. Otherwise, he remains to be active with no fever, good appetite and weight gain. There were no episodes of pneumonia. There has been no history of hospitalization for respiratory exacerbation.

Alternatively, an HPI may be relatively short in length but "extended." For example, the following excerpt is relatively short (e.g., shorter than the excerpt above) but includes enough elements to be an "extended" HPI:

RIH Urinary tract symptoms year old male complaining of pain, discomfort and the presence of an enlarging mass/bulge on his RIGHT inguinal region. He has noted more discomfort and was referred by his primary care physician for evaluation and advice Denies trauma, chills or fever. He has urinary tract symptoms, with penile discomfort, burning sensation and weaker urinary stream.

This HPI contains four elements: location (e.g., RIGHT inguinal region), quality (e.g., pain and discomfort), modifying factors (e.g., denies trauma, chills or fever) and associated signs and symptoms (e.g., urinary tract symptoms, with penile discomfort, burning sensations and weaker urinary stream) and, therefore, is considered an "extended" HPI. Other short in length but extended in content examples can include:

Patient returns for follow up after he underwent a surgical repair of an incarcerated ventral hernia in May 13, 2014. all drains are out now. He states that he is doing well, with minimal complaints.

This is a 78 year old female who presents with venous ulceration. The patient denies pain, drainage, redness, streaking, malodor, fever, chills, night sweats, calf pain, and non-healing wound. It is located on the lateral leg. The ulceration has been present for 3-6 months. Prior care has included compression stockings.

Thus, the length of an HPI, while easy to determine, can be a poor indicator of whether or not an HPI is a "brief" or "extended." An erroneous determination of "brief" or "extended" HPI can result in the HPI being processed incorrectly by an EMR, billing system, care plan, etc., with potential negative impact to patient health and health data processing, and can result in erroneously under-reimbursing (e.g., the HPI should qualify as "extended" but is mis-classified as "brief") or over-reimbursing (e.g., the HPI is mis-classified as "extended" but does not include sufficient information to correctly do so) a provider.

The examples disclosed herein overcome the above obstacles and improve the technology of medical data processing by providing technologically improved systems and methods to normalize an input HPI and classify the HPI using a neural network tuned to process HPI information and generate a classification from the HPI information. In some examples disclosed herein, the HPI is normalized with a natural language processor by tokenizing, lemmatizing, and replacing named entities and medical terms with standardized strings/predefined tags. In some examples disclosed herein, the natural language processor randomly reorganizes the order of each sentence in the input to the HPI. In some examples disclosed herein, the tokens are hashed into integers. In such examples, the integers are representative of an index of a sparse vector where each index represents a distinct word. In examples disclosed herein, the normalized HPI is classified with a neural network. In some examples, the neural network is a three-layer neural network including an embedding layer, recurrent neural network layer, and fully connected layer. In some examples, the recurrent neural network is a long short-term memory (LSTM) network. In some examples, the three-layer neural network outputs a binary output (e.g., a binary classification, either "extended" or "brief" represented as 0 or 1, 1 or 0, etc.) In other examples, the neural network outputs a vector including values corresponding to the presence of each HPI element in an input HPI. In some examples, the output of the neural network can also include a determination of which bodily system(s) is/are discussed in the input HPI. In some examples, the neural network is retrained when a certain number false labels and/or other feedback data are accrued.

Throughout the specification and claims, the following terms take the meanings explicitly associated herein, unless the context clearly dictates otherwise. The term "neural network" refers to a computing system or other processor system that learns to perform a task by analyzing pre-classified training examples. Neural networks include a plurality of densely connected processing nodes inspired by the human brain. In certain examples, the nodes of a neural networks can be organized into layers in which data moves in the forward direction (e.g., data in the first layer moves into the second layer, data in the second layer moves into the third layer, etc.), for example, to drive one or more outputs based on one or more inputs via correlations (e.g., connections) represented by the nodes and their interconnections. Deep learning and/or machine learning can be implemented via a neural network to process incoming data to generate an output and benefit from feedback to improve its processing. A "recurrent neural network" or "RNN" is a type of neural network in which nodes or cells include loops to allow information to persist over time. Thus, the RNN can leverage reasoning about previous events to inform subsequent processing. In an RNN, a memory or other internal state is used to process input sequence(s) in an element-by-element process wherein an output for each element is dependent on the output of previous and/or other elements (e.g., a directed graph driving a sequence).

"Long short-term memory" networks or "LSTM" networks are RNNs designed to handle long-term dependencies. Generally, LSTM networks are organized into cells and gates which interact to optimize the output of the network. Information from outside the processing of the current element (e.g., information from previous elements) is stored in gated cells. These gates release information based on the weight of the gates, which are adjusted and optimized during the training phase of the AI. In an LSTM network (or its pared-down variant gated recurrent unit network), the nodes or cells in the network have storage and an associated stored state under control of the neural network to aid in establishing correlations and processing input data.

FIG. 1 is an illustration of a system in which the teachings of this disclosure may be implemented. An example system 100 includes a data source 102, an HPI classifier 104, and medical support system 106. In the illustrated example, the data source 102 outputs an unprocessed HPI 108 which is transferred to the both the HPI classifier 104 and the medical support system 106. The HPI classifier 104, which is discussed below in greater detail in relation to FIG. 2, classifies the HPI 108 and outputs an HPI classification 110. In some examples, the HPI classification 110 is a binary output of either "brief" or "extended." In the illustrated example, the medical support system 106 links and stores the HPI 108 and the HPI classification 110.

The example data source 102 provides the HPI 108 to the HPI classifier 104. For example, the data source 102 may be database of previously collected and recorded HPIs. Alternatively, in some examples, the data source 102 may be a text input (e.g., a keyboard, a speech to text processor, or a digital scanner with text recognition, etc.). In this example, the data source 102 is used by healthcare professionals, medical support staff, and/or patients to input the HPI. For example, the data source 102 may be a computer terminal in which a healthcare professional records the patient's answers while conducting a medical history. Additionally or alternatively, the data source 102 may contain a user interface which issues prompts asking for particular inputs (e.g., "Where is the pain location?," "How severe is the pain?," "When do the symptoms occur?," etc.). In this example, the data source 102 constructs the HPI 108 from the answers to the provided prompts.

In the illustrated example, the example medical support system 106 is a digital database which contains the medical history of a patient and a summary of the medical encounters of the patient. The example medical support system 106 records both the HPI 108 and the HPI classification 110. The example medical support system 106 can be any suitable medical system (e.g., an EMR, a medical billing system, etc.). For example, the medical support system 106 may store the HPI 108 as a text string associated with the patient's related medical encounter. Alternatively, the HPI 108 may recorded in any suitable method (e.g., each word of the HPI is stored as separate string, etc.). In some examples, the HPI classification 110 is stored as an associated binary value to the HPI 108. Alternatively, in some examples, the HPI classification 110 and the HPI 108 may be concatenated together, such that the HPI classification 110 is added to the text string of the HPI 108. In this example, the HPI 108 and HPI classification 110 are stored as a single text string. Alternatively, the HPI classification 110 may be stored by any suitable method.

Figure 2:
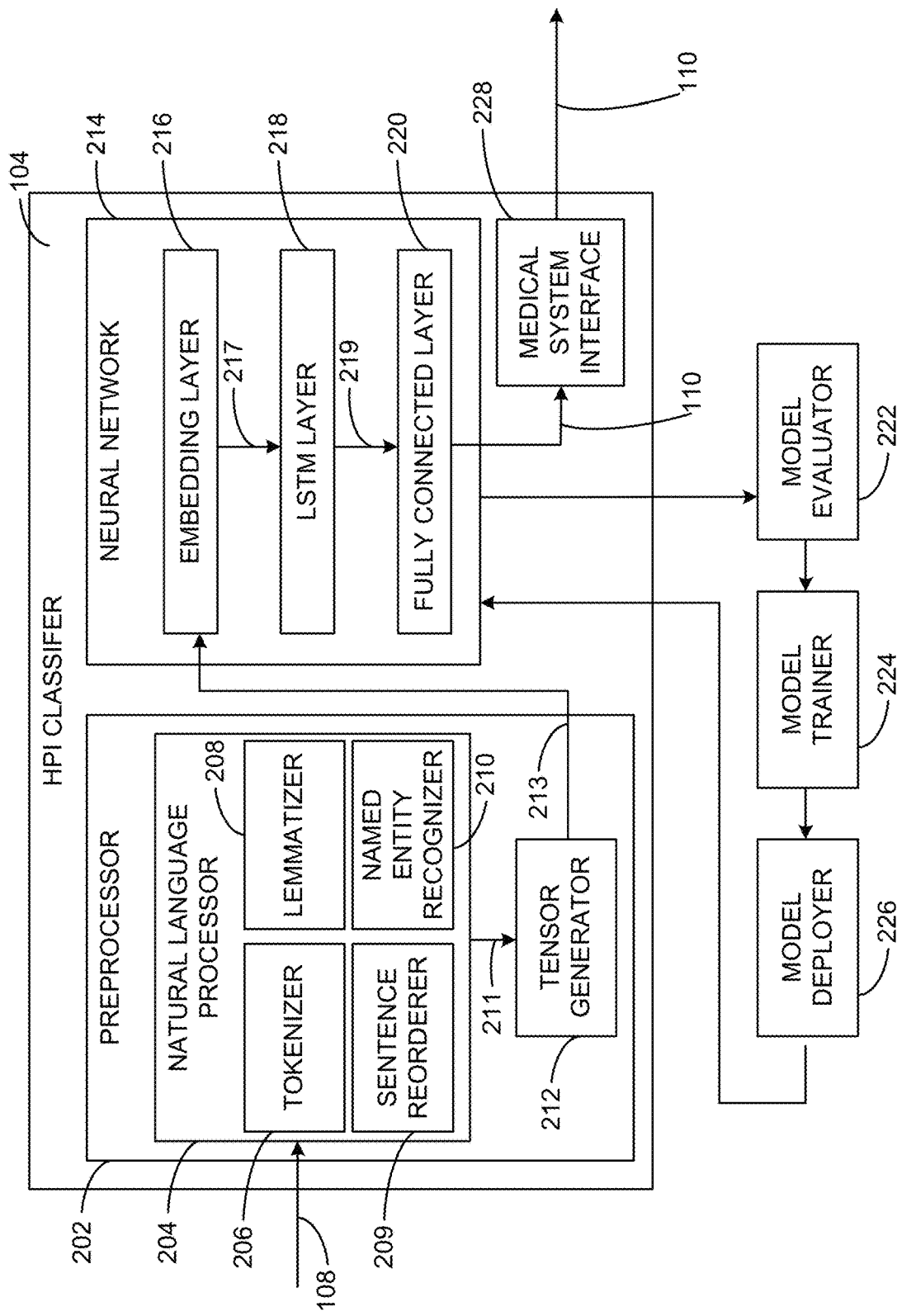
FIG. 2 is a block diagram representative of the HPI classifier of FIG. 1.

FIG. 2 is a block diagram depicting the HPI classifier 104 of FIG. 1 in greater detail. The HPI classifier 104 includes an example preprocessor 202 and an example neural network 214. The example preprocessor 202 includes an example natural language processor 204 and an example tensor generator 212. The example natural language processor 204 includes an example tokenizer 206, an example lemmatizer 208, an example sentence reorderer 209 and an example named entity recognizer 210. The example neural network 214 includes an embedding layer 216, an example LSTM layer 218 and an example fully connected layer 220. Additionally, in some examples, the neural network 214 has auxiliary elements to retrain including an example model evaluator 222, an example model trainer 224 and an example model deployer 226. In some examples, the example HPI classifier 104 includes a medical system interface 228.

The HPI classifier 104 receives the unprocessed HPI 108 (e.g., from the data source 102 of FIG. 1). In the illustrated example, the HPI 108 is preprocessed by the preprocessor 202 beginning in the natural language processor 204. For example, when the HPI 108 is received by the natural language processor 204, the example sentence reorderer 209 shuffles the order of each sentence of the HPI 108 around into a random order. In some examples, reshuffling the order of the sentences of the HPI 108 prevents the order of sentences from effecting the output of the neural network 214. In some examples, because the classification of the HPI 108 is only dependent on the presence of the seven elements and not the ordering of the elements, this removes any potential unintentional effects that sentence ordering may have on the HPI classification 110.

The tokenizer 206 converts each word or group of words of the HPI 108 into a token. In some examples, the tokenizer 206 breaks the input HPI 108 string into individual tokens. For example, if the tokenizer 206 encounters the sentence "the quick brown fox jumps over the lazy dog," the tokenizer 206 would tokenizer the sentence into "the," "quick," "brown," "fox," "jumps," "over," "the," "lazy," and "dog." In some examples, the tokenizer 206 tokenizes the HPI 108 based on a "space" delimiter (e.g., " "). In other examples, the tokenizer 206 can tokenize the HPI 108 based on another character, rule, etc. For example, the tokenizer 206 can have special-case rules which allow for certain types of phrases to be tokenized together. For example, if a date (e.g., "Mar. 12, 2018") is encountered, the tokenizer 206 can tokenize the date into a single token. Additional examples include, the tokenizer 206 can tokenize names and titles together (e.g., "Dr. Smith") and/or certain medical abbreviations (e.g., "obstructive sleep apnea," "cardiac arrest," and "Type 2 diabetes."). Additionally or alternatively, the tokenizer 206 can tokenize short phrases together based on simple rules. For example, the tokenizer 206 can group together numbers and words following them together (e.g., "4 hours," and "five ounces"). In some examples, multiword phrases indicating locations can similarly be tokenized together (e.g., "St. George's Hospital" and "Chicago, Ill.").

The example named entity recognizer 210 scans the tokenized HPI 108 for numbers, dates, named entities, medical terms, abbreviations, and/or misspelling and replaces these elements with standardized tokens. For example, if the named entity recognizer 210 identifies the token "Dr. Smith", the named entity recognizer 210 replaces the token with a standardized indication token such as "PERSON." For example, if the named entity recognizer 210 identifies the token "Mar. 12, 2018", the named entity recognizer 210 replaces the token with a token saying "DATE." Alternatively, the token "Mar. 12, 2018" is replaced with three tokens representing month, day and year, namely "DATE," "DATE," and "DATE," respectively. For example, if the named entity recognizer 210 identifies the token "St. George's Hospital", the named entity recognizer 210 replaces the token with a standardized token such as "FACILITY." For example, if the named entity recognizer 210 identifies the token "4 Hours", the named entity recognizer 210 replaces the token with a standardized token such as "TIME." For example, if the named entity recognizer 210 identifies the token "five ounces", the named entity recognizer 210 replaces the token with a token such as "QUANTITY." For example, if the named entity recognizer 210 identifies the token "Chicago, Ill.", the named entity recognizer 210 replaces the specific token with a standardized token such as "LOC", "LOCATION", etc.

In some examples, the named entity recognizer 210 can replace medical abbreviations, abbreviations and misspellings with a standardized token representing words that are out of vocabulary (e.g., OOV, etc.). In some examples, out of vocabulary words are referenced to a dictionary. In other examples, the named entity recognizer 210 may have a separate token for medical terms and abbreviations (e.g., "MED."). In this example, the example HPI classifier 104 includes a medical dictionary (e.g., Radlex, LOINC, SNOMED, CPT, ICD-10, etc.). In some examples, the named entity recognizer 210 can replace medical terms and abbreviations with more specific tokens (e.g., separate tokens for medical procedures, medicines and diseases, etc.). For example, the named entity recognizer 210 can replaced medical terms and abbreviations with tokens relating to specific bodily systems (e.g., "heart stent" could be replaced with a token reflecting a circulatory procedure (e.g., "CIR PRO," etc.)).

The example lemmatizer 208 receives the tokens from the named entity recognizer and replaces each token with a lemma associated with the respective token. As used herein, a "lemma" is the dictionary form of a word. In some examples, the lemmatizer 208 replaces inflected verbs with a related base verb. For example, if the lemmatizer 208 encounters token "am," "are," or "is," the lemmatizer 208 can replace the token with "be." Additionally or alternatively, the lemmatizer 208 can similarly replace inflected noun tokens (e.g., "cars," "cars'," "car's," etc.) with their related lemma (e.g., car). In some examples, the lemmatizer 208 can have similarly functionality with other types of words. In some additional examples, the lemmatizer 208 can use a word's context to determine its proper lemma. For example, the word "drawer" can have the lemma "drawer" if the word is user a noun or "draw" if the word is used as a verb. In some examples, the lemmatizer 208 reduces the required complexity of the neural network by reducing the possible number of inputs the network can receive.

In some examples, the natural language processor 204 outputs a preprocessed HPI 211. In some examples, the lemmatizer 208, sentence reorderer 209, and the named entity recognizer 210 may not be components within the natural language processor 204. In these examples, the preprocessed HPI 211 may not be lemmatized, reordered or have its named tokens replaced with standardized or other predefined tags. Alternatively, any suitable type of preprocessing can be performed to generate the preprocessed HPI 211.

The example tensor generator 212 receives the tokenized HPI 211. The example tensor generator 212 receives the tokenized HPI 211 and outputs a tensor 213. In some examples, the tensor generator 212 converts each token of the tokenized HPI 211 into a vector. In some examples, the vector is a binary sparse vector in which one dimension (e.g., one index) has a value of "1" and each of the other dimensions are "0." In some examples, each dimension of the vector represents a different possible token. For example, if the tokenized HPI 211 can be composed from any number of 50,000 different tokens, each vector has 50,000 different dimensions. In this example, if the tokenized HPI 211 is one hundred tokens in length, the tensor generator 212 vectorizes each of the one hundred tokens into a vector. In some examples, the example tensor 213 includes each of these vectors concatenated (e.g., "stacked", appended, etc.) together. In some examples, to save memory, the tensor generator 212 vectorizes each token into a scalar value representing the would-be index of sparse value of the associated vector. In this example, the tensor 213 is a vector of these scalar values.

In the illustrated example, the example tensor 213 is input into the neural network 214. In the illustrated example, the neural network 214 is an LSTM network. Alternatively, the neural network 214 can be implemented using a general RNN, recursive neural network, or any other suitable type of machine learning architecture. In some examples, the neural network 214 can be a part of a larger and/or more complex neural network with additional functions (e.g., identifying the bodily system described in HPI, etc.). In the illustrated example, the neural network 214 outputs a binary output (e.g., the HPI classification 110). In other examples, the output of the neural network 214 can indicate the presence of particular HPI elements (e.g., a location of problem, a quality of problem, etc.) in the input HPI 108.

In the illustrated example, the first layer of the neural network 214 is an embedding layer 216 to prepare tensor(s) 213 for processing by the layers of the neural network 214. In the illustrated example, the embedding layer 216 converts each vectorized token of the tensor 213 into a dense vector corresponding to that token. In some examples, the number of dimensions of the embedding layer 216 corresponds to the length of the dense vector created by the embedding layer 216. In some examples, adding more dimensions to the embedding layer 216 increases the accuracy and robustness of the neural network 214. In some examples, each unique sparse vector of the tensor 213 is embedded to a specific corresponding dense vector by the embedding layer 216. For example, if the same vector (e.g., [522]) appears twice in the tensor, that sparse vector is mapped to the same dense vector. In some examples, the specific values of the dimensions of the embedded dense vectors are optimized during the training process of the neural network 214. The embedded dense vectors 217 are input to the LSTM layer 218 of the neural network. Thus, for example, a 2D tensor can be transformed into a 3D tensor via the embedding layer 216 as input to the RNN to determine a feature output (e.g., brief/extended, etc.).

The example LSTM layer 218 receives the embedded dense vectors 217 output by the embedding layer 216 and outputs a single output vector 219 of a predetermined length. In some examples, the dimensions of the LSTM layer 218 correspond to the length of the output vector 219. In some examples, the LSTM layer 218 uses a soft-sign activation function. Alternatively, any suitable activation function may be used (e.g., a hyperbolic tangent (tan h) activation function, etc.). In some examples, the operations of the LSTM layer 218 are optimized during the training of the neural network 214. The LSTM layer 218 leverages history or learned recognition of language, words, phrases, patterns, etc., in the input vectors 217 using information stored in recurrent gates from prior visible and/or hidden cells in the LSTM layer 218 to arrive at the output vector 219 based on the combination of information in the vector(s) 217. An LSTM unit in the LSTM layer 218 receives input state, hidden state, and cell state information and processes the input information using one or more gates including sigmoid, hyperbolic tangent, etc., to apply weighted and/or unweighted element-wise addition and/or multiplication to the vector elements and produce an output state. Via the LSTM 218, some information can be stored and/or conveyed from one cell to another via the output state and other information can be discarded or "forgotten" to rid the model of old or outdated information.

The output vector 219 of the LSTM layer 218 is input into the fully connected layer 220. In the illustrated example, the fully connected layer 220 has a single dimension with a binary output indicating if the HPI 108 is "brief" or "extended." Alternatively, if the neural network 214 has additional outputs (e.g., determining which bodily system, such as endocrine system, renal system, etc., is described in the HPI, the presence of particular HPI elements, etc.), the fully connected layer 220 can have additional dimensions. In the illustrated example, the fully connected layer 220 uses a sigmoid activation function. In some examples, the output vector of the LSTM layer 218 is linearized by matrix multiplication. In this example, this scalar value is then rounded to either "0" or "1," which are associated with either "brief" or "extended," respectively. In the illustrated example, the binary output value generated by the fully connected layer 220 is the HPI classification 110. In other examples, the fully connected layer 220 can generate the HPI classification 110 by any other suitable function. In some examples, the function of the fully connected layer 220 is optimized during the training of the neural network 214.

In the illustrated example, the neural network 214 can be periodically retrained (e.g., based on a threshold of feedback, at the discretion of an operator of the system, quarterly, etc.). In some examples, the neural network is automatically retrained after a certain threshold of incorrectly classified HPIs are accumulated (e.g., a model evaluator 222 determines that too many HPIs have been mis-classified so the model should be updated to improve classification accuracy, etc.). To retrain the neural network 214, the model evaluator 222, a model trainer 224 and a model deployer 226 are used. The example model evaluator 222 monitors and evaluates the output HPI classifications 110 of the neural network 214. In some examples, if a healthcare professional notices and records an incorrect HPI classification 110, the model evaluator 222 notes the error of the misclassified HPI 108 along with the correct HPI classification. In some examples, another system and/or application, such as a billing system, computer-aided diagnosis system, quality control processor, etc., flags and/or otherwise identifies an incorrect HPI classification 110, which can be noted by the model evaluator 222 along with the correct classification. In some examples, the model evaluator 222 can monitor a government and/or third-party process that rejects an HPI and/or associated medical record due to HPI misclassification. In some examples, when the model evaluator reaches a threshold in of feedback, the model evaluator 222 triggers or otherwise instructs the model trainer 224 to begin training a new neural network (e.g., to replace the deployed neural network model/construct 214). Additionally or alternatively, the model evaluator 222 can periodically (e.g., quarterly, yearly, etc.) trigger the model trainer 224 to begin training a new neural network. In some examples, the model evaluator 222 also monitors for positive feedback (e.g., a human, system, process, etc., verifying that an HPI was correctly classified and can be used).

The example model trainer 224 trains a new, updated, or different neural network model/other construct to replace the currently deployed neural network 214. For example, the model trainer 224 can use the positive or/and negative feedback compiled by the model evaluator 222 to create a new data set of HPIs to train and/or test the new neural network. In some examples, the model trainer 224 can use previous training/testing data (e.g., pre-classified HPIs used to train the neural network 214) in conjunction with the newly constructed training/testing data set (e.g., pre-classified HPIs not used to train the neural network 214). In some examples, the model trainer 224 iteratively varies a strength of connection between the nodes/units of the neural network until the newly trained model set achieves a desired accuracy (e.g., the new neural network correctly classifies the previously incorrectly classified HPIs of the training set). In some examples, the model train then uses a separate test set of HPIs to validate the accuracy of the newly trained neural network. If the result of this validation satisfies specified criterion(-ia), the model trainer 224 outputs the newly trained neural network to the model deployer 226. The example model deployer 226 deploys the trained neural network model. For example, the model deployer 226 makes the strength of connections between nodes of the neural network rigid (e.g., not able to change). Once the model deployer 226 has made the newly trained neural network static, the model deployer 226 replaces the neural network 214 with the newly trained neural network as the deployed neural network 214 (e.g., the deployed model) to be used in classification of incoming medical data.

The example medical system interface 228 modifies a medical support system (e.g., the medical support system 106 of FIG. 1) with the HPI classification 110. In some examples, the example medical system interface 228 may trigger a response from the medical support system 106. For example, if the medical support system 106 is an EMR, the medical system interface 228 may cause the HPI classification 110 to be associated with a patient's medical history. In other examples, if the medical support system 106 is a medical billing system, the medical system interface 228 may trigger a medical bill to be generated based on the classified HPI (e.g., a more expensive bill may be issued if the HPI classification 110 is an extended).

Figure 4:
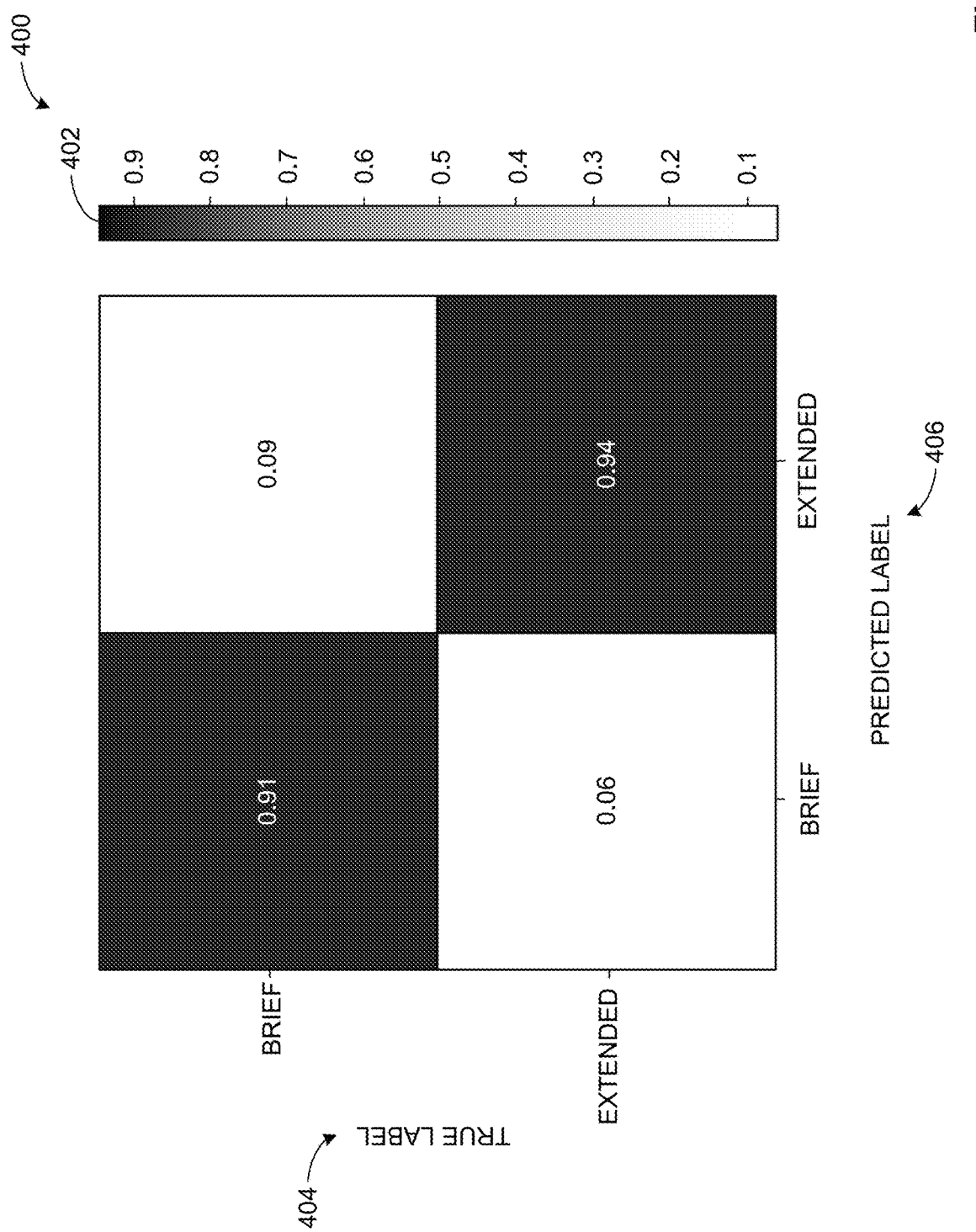
FIG. 4 is an example confusion table of a group of HPIs submitted to a trained HPI classifier.

While an example implementation of the HPI classifier 104 of FIG. 1 is illustrated in FIG. 2, one or more of the elements, processes, and/or devices illustrated in FIG. 4 can be combined, divided, re-arranged, omitted, eliminated, and/or implemented in any other way. Further, the example preprocessor 202, the example natural language processor 204, the example tokenizer 206, the example lemmatizer 208, the example sentence reorderer 209, the example named entity recognizer 210, the example tensor generator 212, the example neural network 214, the example embedding layer 216, the example LSTM layer 218, the example fully connected layer 220, the medical system interface 228 and/or, more generally, the example HPI classifier 104 of FIG. 1 can be implemented by hardware, software, firmware, and/or any combination of hardware, software, and/or firmware. Thus, for example, any of the example preprocessor 202, the example natural language processor 204, the example tokenizer 206, the example lemmatizer 208, the example sentence reorderer 209, the example named entity recognizer 210, the example tensor generator 212, the example neural network 214, the example embedding layer 216, the example LSTM layer 218, the example fully connected layer 220, and/or, more generally, the example AI can be implemented by one or more analog or digital circuit(s), logic circuits, programmable processor(s), programmable controller(s), graphics processing unit(s) (GPU(s)), digital signal processor(s) (DSP(s)), application specific integrated circuit(s) (ASIC(s)), programmable logic device(s) (PLD(s)), and/or field programmable logic device(s) (FPLD(s)). When reading any of the apparatus or system claims of this patent to cover a purely software and/or firmware implementation, at least one of the example, example preprocessor 202, the example natural language processor 204, the example tokenizer 206, the example lemmatizer 208, the example sentence reorderer 209, the example named entity recognizer 210, the example tensor generator 212, the example neural network 214, the example embedding layer 216, the example LSTM layer 218, the example fully connected layer 220, the medical system interface 228 is/are hereby expressly defined to include a non-transitory computer readable storage device or storage disk such as a memory, a digital versatile disk (DVD), a compact disk (CD), a Blu-ray disk, etc., including the software and/or firmware. Further still, the example HPI classifier 104 of FIG. 1 can include one or more elements, processes, and/or devices in addition to, or instead of, those illustrated in FIG. 2, and/or may include more than one of any or all of the illustrated elements, processes, and devices. As used herein, the phrase "in communication," including variations thereof, encompasses direct communication and/or indirect communication through one or more intermediary components, and does not require direct physical (e.g., wired) communication and/or constant communication, but rather additionally includes selective communication at periodic intervals, scheduled intervals, aperiodic intervals, and/or one-time events.

Flowcharts representative of example hardware logic or machine readable instructions for implementing the HPI classifier 104 of FIG. 1 are shown in FIGS. 6-9. The machine readable instructions can be a program or portion of a program for execution by a processor such as the processor 1012 shown in the example processor platform 1100 discussed below in connection with FIG. 10. The program can be embodied in software stored on a non-transitory computer readable storage medium such as a CD-ROM, a floppy disk, a hard drive, a DVD, a Blu-ray disk, or a memory associated with the processor 1012, but the entire program and/or parts thereof can alternatively be executed by a device other than the processor 1012 and/or embodied in firmware or dedicated hardware. Further, although the example programs are described with reference to the flowcharts illustrated in FIGS. 6-9, many other methods of implementing the example HPI classifier 104 can alternatively be used. For example, the order of execution of the blocks can be changed, and/or some of the blocks described can be changed, eliminated, or combined. Additionally or alternatively, any or all of the blocks can be implemented by one or more hardware circuits (e.g., discrete and/or integrated analog and/or digital circuitry, an FPGA, an ASIC, a comparator, an operational-amplifier (op-amp), a logic circuit, etc.) structured to perform the corresponding operation without executing software or firmware.

As mentioned above, the example processes of FIGS. 6-9 can be implemented using executable instructions (e.g., computer and/or machine readable instructions) stored on a non-transitory computer and/or machine readable medium such as a hard disk drive, a flash memory, a read-only memory, a compact disk, a digital versatile disk, a cache, a random-access memory, and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media.

"Including" and "comprising" (and all forms and tenses thereof) are used herein to be open ended terms. Thus, whenever a claim employs any form of "include" or "comprise" (e.g., comprises, includes, comprising, including, having, etc.) as a preamble or within a claim recitation of any kind, it is to be understood that additional elements, terms, etc. may be present without falling outside the scope of the corresponding claim or recitation. As used herein, when the phrase "at least" is used as the transition term in, for example, a preamble of a claim, it is open-ended in the same manner as the term "comprising" and "including" are open ended. The term "and/or" when used, for example, in a form such as A, B, and/or C refers to any combination or subset of A, B, C such as (1) A alone, (2) B alone, (3) C alone, (4) A with B, (5) A with C, and (6) B with C.

Figure 3:
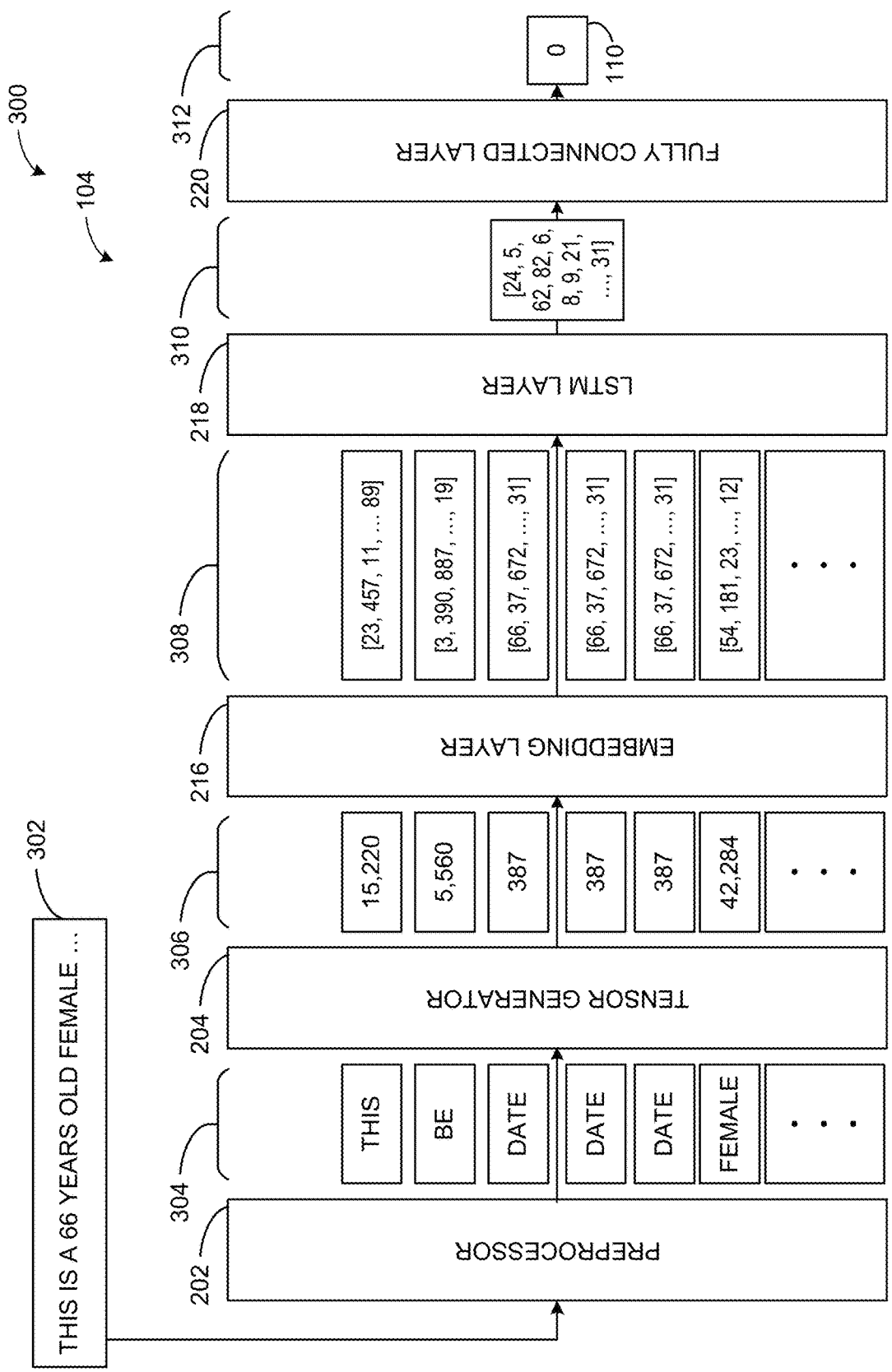
FIG. 3 is an example data flow of an HPI through the HPI classifier of FIG. 2.

FIG. 3 depicts an example data flow diagram 300 of an HPI 302 through the HPI classifier 104 of FIGS. 1 and 2. In the illustrated example, the example HPI 302 (e.g., the narrative HPI 108 of FIG. 2) is input to the HPI classifier 104. In this example, the example HPI 302 begins with the phrase "THIS IS A 66 YEARS OLD FEMALE." Once received by the HPI classifier 104, the HPI 302 is received by the preprocessor 202. The preprocessor 202 converts the example HPI 302 into an example preprocessed HPI 304. To create the preprocessed HPI 304, the preprocessor 202 can tokenize the HPI 302 (e.g., using the tokenizer 206), lemmatize the HPI 302 (e.g., using the lemmatizer 208), reorder the sentences of the HPI 302 (e.g., using the sentence reorderer 209), and/or replace named entities recognized in the HPI 302 (e.g., using the named entity recognizer 210). For example, the beginning phrase "THIS IS A 66 YEARS OLD FEMALE" of the HPI 302 is tokenized into "THIS," "IS," "66" "A YEARS" "OLD," and "FEMALE" by the tokenizer 206. In the illustrated example, the lemmatizer 208 then replaces the "IS" token with the token's lemma, "BE." Additionally, the named entity recognizer then replaces each of "66," "A YEARS," and "OLD" with a named entity token of "DATE." The beginning phrase of the example HPI 302 has been preprocessed into the example preprocessed HPI 304 that includes the tokens "THIS," "BE," "DATE," "DATE," "DATE," and "FEMALE." The preprocessed HPI 304 is then sent to the tensor generator 212.

At the tensor generator 212, the preprocessed HPI 304 is converted into an example sparse tensor 306. In the illustrated example, each token of the preprocessed HPI is one-hot encoded into a sparse vector. For example, if the number of possible tokens than included in the preprocessed HPI is 50,000, each sparse vector is 50,000 dimensions in length. In the illustrated example, to save memory, each sparse vector is stored as a scalar value in the example tensor 306 where each scalar value represents the dimension of the sparse vector. For example, the token "THIS" is associated with the 15,220th dimension of the sparse vector and is stored in the example tensor 306 as "15,220." The tokens "BE" and "FEMALE" are similarly stored as "5,560" and "42,284" respectively. Additionally, because each possible dimension of the sparse vectors is associated with a specific token, each of the "DATE" tokens is stored as "387" in the sparse tensor 306. Once each token has been converted into a sparse vector and added to the example sparse tensor 306, the sparse tensor 306 is input into the embedding layer 216.

At the embedding layer 216, each element of the sparse tensor 306 is converted into an example dense tensor 308. In the illustrated example, each element of the example sparse tensor 306 (e.g., the sparse vectors) is embedded into a corresponding dense vector. In some examples, the mathematical process of this conversion is optimized during the training of the model (e.g., the neural network 214 of FIG. 2). In the illustrated example, repeat elements of the sparse tensor 306 (e.g., "387") are embedded as the same dense vector (e.g., [66, 37, 672, . . . , 31]). In some examples, a length of each of the vectors in the dense vector 308 is equal to a number of dimensions in the embedding layer 216. Once the dense vector 308 has been generated, the dense vector 308 is input into the LSTM Layer 218.

The example LSTM Layer 218 converts the dense vector 308 into an output vector 310 using a softsign activation function. In some examples, the mathematical process of this conversion is optimized during the training of the model (e.g., the neural network 214 of FIG. 2). In some examples, the length of the output vector 310 corresponds to the number of dimensions of the LSTM layer 218. The example output vector 219 is then input into the fully connected layer 220. The example fully connected layer 220 linearizes the example output vector 310 into an example binary output 312 using a sigmoid function. In some examples, the binary output 312 corresponds to the HPI classification 110.

FIG. 4 shows an example confusion table 400 which includes example results of a group of human classified HPIs classified using by a deployed HPI classifier 104 of FIG. 1. A confusion table is a metric used to visualize performance of an algorithm or neural network. In the illustrated example, a grading index 402 depicts a greyscale gradient of example percentages the results can have. A y-axis 404 represents the "True Label" (e.g., labeled by humans) of an HPI, and an x-axis 406 represents the "Predicted Label" of HPI as classified by the HPI classifier 104. In the illustrated example, 91% of "brief" HPIs were correctly classified as such by the HPI classifier 104 whereas 9% were incorrectly classified as "extended." Similarly, in the illustrated example, 6% of "extended" HPIs were erroneous classified as "brief" by the HPI classifier 104 whereas 94% were correctly classified as "extended."

Figure 5:
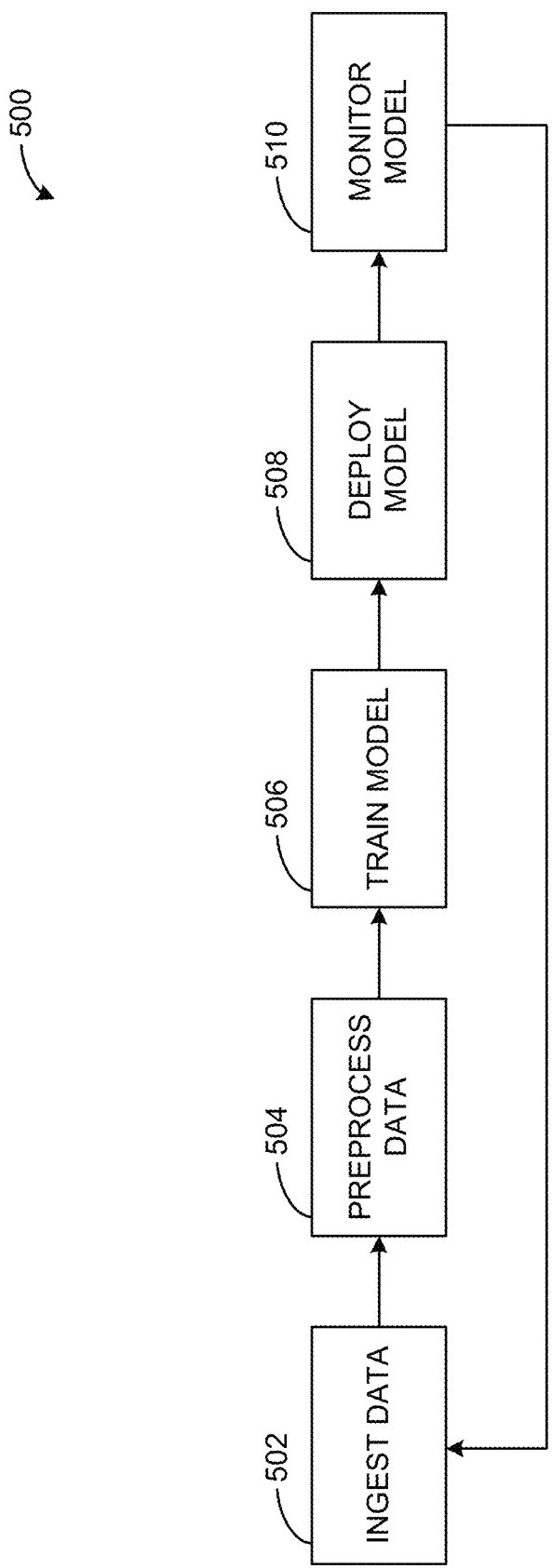
FIG. 5 is a process flow diagram that can be implemented to deploy a model to be used to process incoming patient data.

FIG. 5 is a process flow diagram of an example process 500 to deploy the HPI classifier 104 of FIG. 1 to be used to classify incoming patient HPIs. The process 500 begins at block 502. At block 502, the data source 102 ingests a set of preclassified HPIs to be used to train the neural network (e.g., the neural network 214 of FIG. 2) of the HPI classifier 104. In some examples, each HPI of the set of HPIs is classified by a healthcare professional prior to being ingested by the data source 102. In this example, the HPI classification 110 is ingested with the example HPI 108. At block 504, the preprocessor 202 preprocesses the ingested data. Additional detail in the function of the preprocessor is provided below in conjunction with FIG. 7. In some examples, the preprocessor 202 also preprocesses the HPI classification 110.

At block 506, the model (e.g., the neural network 214) is trained using the preprocessed HPI(s) 108 and HPI classification(s) 110 (e.g., collectively referred to as the samples). In some examples, the samples are processed iteratively in epochs until the model converges. In some examples, the samples are divided such that are some of the samples are used for training and some are used for validation (e.g., confirming the model works after training). Known outcomes/results can be used to verify performance of the training model, which can also be validated with a test data set. In some examples, a set of known, "gold standard", "truthed", or other reference data can be divided into a training data set to train the model and a test data set to test the trained network model to validate its correct operation. After the model has been trained and validated, the process 500 advances to block 508.

At block 508, the model is deployed. In some examples, the model is deployed as application within a medical support system (e.g., the medical support system 106 of FIG. 1), billing software, computer-aided diagnosis (CAD) application, etc. In other examples, the model is a standalone application. In some examples, when the process 500 is being used to retrain the model, the model is to replace a previously used model so a prior deployed model is replaced with the newly deployed model in the target system.

At block 510, after the model has been deployed, the model evaluator 222 monitors the monitor for potential misclassifications. In some examples, the model evaluator keeps a database of improperly classified HPIs. Classified HPIs can be confirmed as properly or improperly classified through user feedback, other system evaluation (e.g., a billing system determines that an HPI is not in fact extended, etc.), etc. Such feedback can be used to trigger a subsequent retraining of the model (e.g., when a number or percentage or improper classifications reaches or exceeds a threshold, criterion, etc.), for example.

Figure 6:
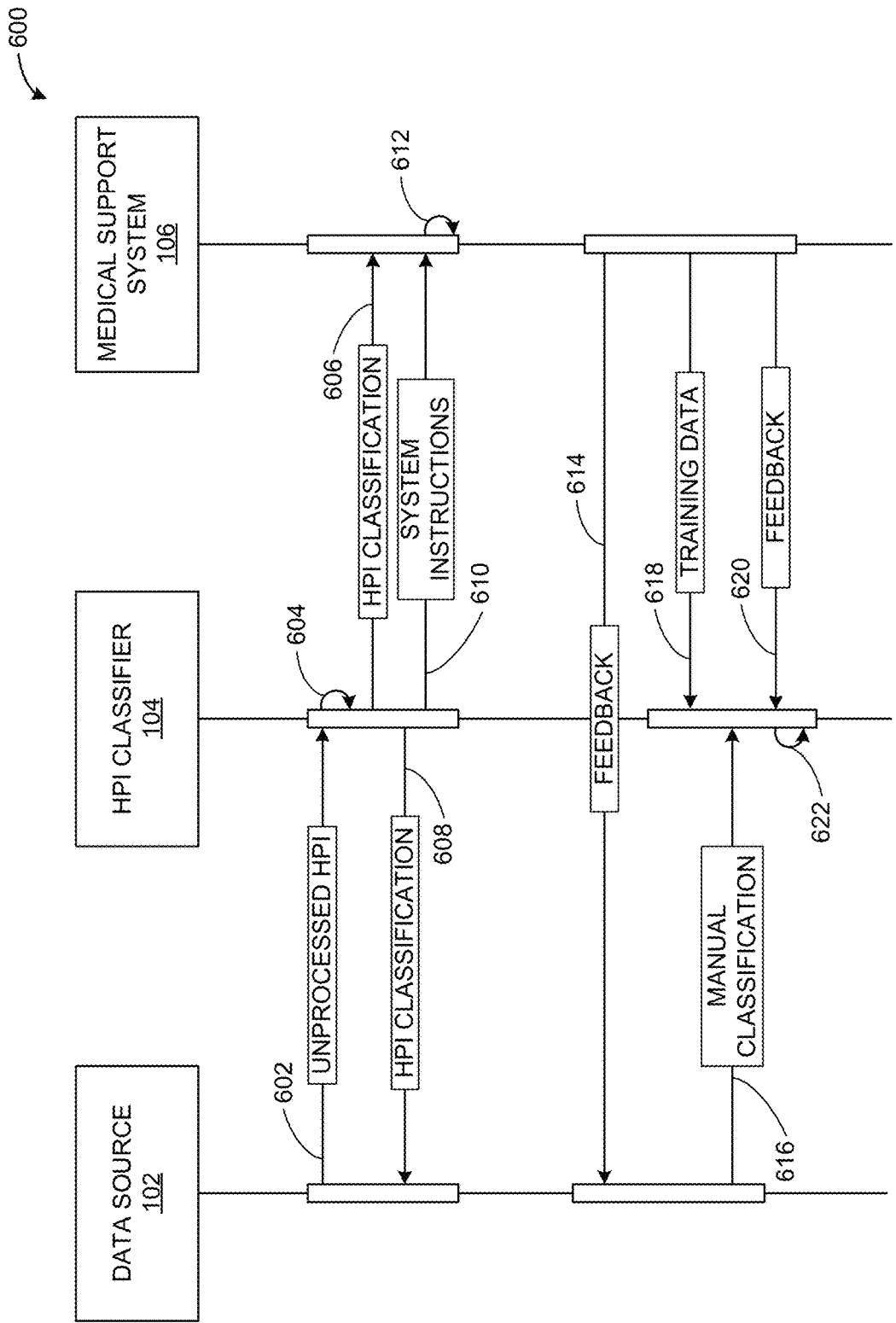
FIG. 6 is an illustration of an example data flow and transformation of information flowing through components of the example system of FIG. 1.

FIG. 6 is an illustration of an example data flow and transformation of information 600 flowing through the example data source 102, the example HPI classifier 104 and the example medical support system 106 of the example system of FIG. 1. As shown in the illustrated example, an example transmission 602 (e.g., a message, an instruction, a data packet, etc.) is sent from the data source 102 to the example 604. The example transmission 602 includes an unprocessed HPI (e.g., the HPI 108 of FIG. 1). Additionally or alternatively, the example transmission can include any other suitable information (e.g., information about the data source 102, about an associate patient, etc.). The example HPI classifier 104 can use the data included in the transmission 602 to execute an example action 604. The example action 604 can include classifying the unprocessed HPI of the transmission 602. In response to the action 604, the HPI classifier 104 can transmit an example transmission 606 including an HPI classification to medical support system 106 and/or an example HPI classification message 608 back to the data source 102.

More specifically, as shown in the example of FIG. 6, the example transmission 606 and the example transmission 608 include an HPI classification. In some examples, the transmission 606 and/or the example transmission 608 can further include the HPI 108. The example transmission 608 can notify the data source 102 of the HPI classification generated by the HPI classifier 104. The example HPI classifier 104 can also transmit an example transmission 610. In the illustrated example, the example transmission 610 can include system instructions that can cause the medical support system 106 to undergo an example action 612. For example, the action 612 can include generating a bill and/or insurance claim. Additionally or alternatively, the medical system interface 220 can cause the medical support system 106 to generate, update or delete a medical record. In some examples, the action 612 can include generating, updating or deleting a medical record. In some examples, the action 612 can include generating a request or reminder for an appointment. Additionally or alternatively, the action 612 can trigger any other suitable action from the medical support system 106 such as schedule an imaging exam, schedule a laboratory test session, trigger a reminder for clinician follow-up, configure an imaging workstation and/or other clinician computing device for patient data analysis, etc.

The medical support system 106 can further send an example transmission 614 to the data source 102. The example transmission 614 can include feedback (e.g., a notification of whether the HPI classification was correct, etc.) for the medical support system 106. The example transmission 614 can further include a request to manually classify one or more HPIs that can also be included in the example transmission 614. The example transmission 614 can trigger the data source 102 to send an example transmission 616. The example transmission 616 can include, for example, a manual classification of an HPI included in the example transmission 614. The medical support system 106 can further transmit an example transmission 618. In the illustrated example, the example transmission 618 can include training data to be used to by the HPI classifier 104. For example, the example transmission 618 can include unclassified HPIs stored in the medical support system 106 and/or incorrectly classified HPIs (e.g., incorrectly classified by the HPI classifier 104, incorrectly manually classified, etc.).

The medical support system 106 can further transmit an example transmission 620 to the HPI classifier 104. In the illustrated example, the example transmission 620 can include feedback from the medical support system 106 to the HPI classifier 620. In some examples, the example transmission 620 can trigger an example action 622. The example action 622 can include retraining the neural network (e.g., the neural network 214 of FIG. 2) of the HPI classifier 104 and can, for example, include executing the process 500 of FIG. 5. Thus, for example, based on feedback received from the medical support system 106 and/or the data source 102 (e.g., negative feedback regarding incorrect classification results, etc.), the HPI classifier 104 can be triggered to regenerate the network model 300 to be redeployed for further HPI classification, etc.

Figure 7:
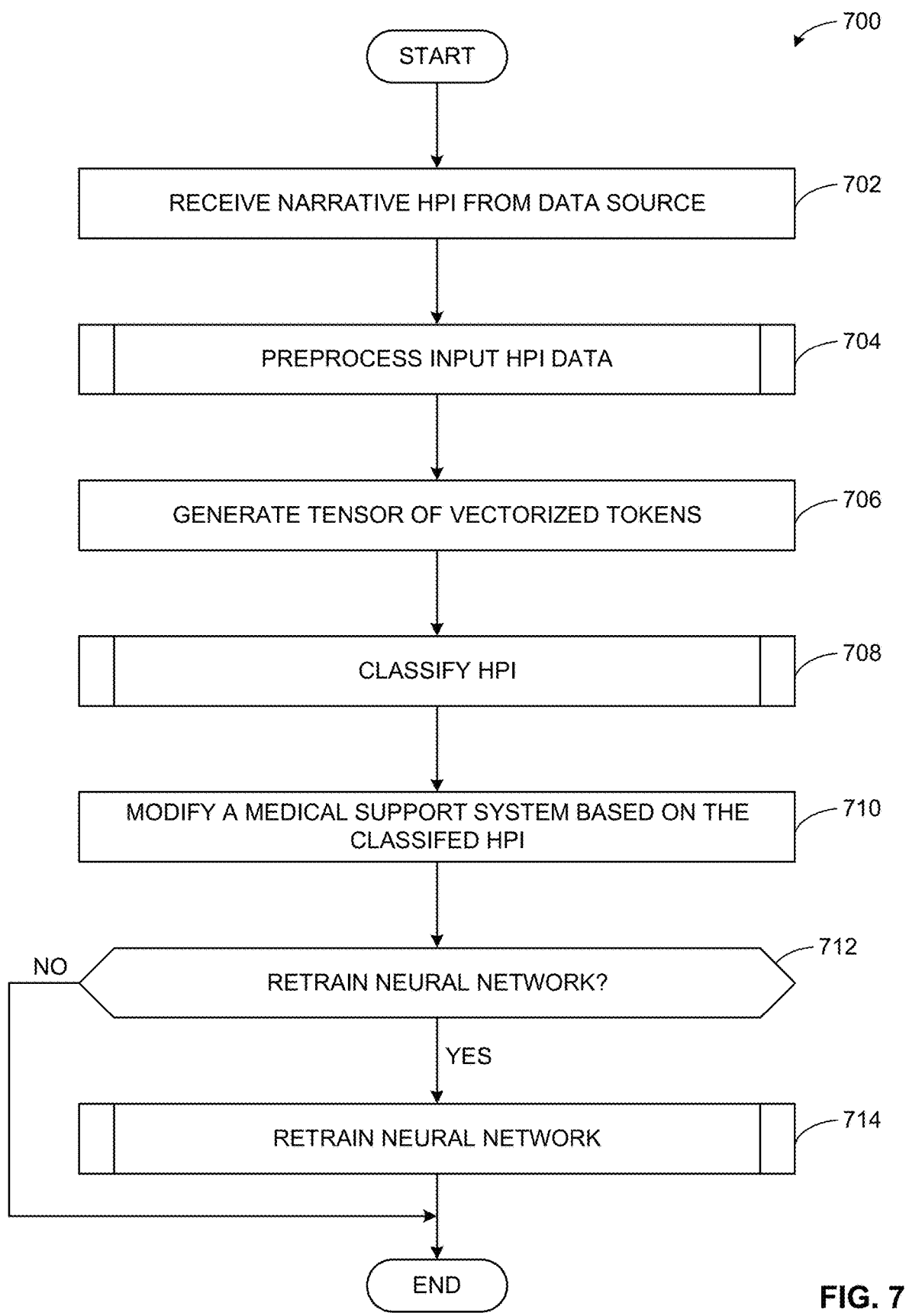
FIG. 7 is a flowchart representative of machine readable instructions which can be executed to implement the HPI classifier of FIG. 2.

FIG. 7 is a flowchart representative of machine readable instructions 700 which can be executed to implement the HPI classifier of FIG. 2. The process 700 of FIG. 7 begins at block 702. At block 702, the preprocessor 202 receives the narrative HPI 108 from the data source 102. In some examples, the narrative HPI 108 is retrieved from a database of HPIs. In other examples, the HPI 108 is input by a patient or healthcare professional after conducting a medical with the patient. Alternatively, the HPI 108 can be retrieved from any suitable source. In some examples, the HPI 108 is formatted as one continuous text string. Alternatively, the HPI 108 can be formatted in any way readable by the preprocessor 202. Once the HPI 108 has been retrieved, the process 700 advances to block 704.

At block 704, the preprocessor 202 preprocesses the HPI 108. Additional detail in the execution of block 704 is provided below in conjunction with FIG. 8. After the HPI 108 has been preprocessed into the tokenized HPI 211, the process advances to block 706 at which the tensor generator 212 generates a tensor 213 of vectorized tokens. For example, the tensor generator 212 can map each of the tokens of the tokenized HPI 108 into a sparse vector and forms a tensor 213 by concatenating each of the sparse vectors. Alternatively, the tensor generator can map each the tokens of the tokenized HPI 211 into a scalar value, which corresponds to the dimension of the sparse vector that token would be mapped to. In this example, the tensor generator 212 generates a vector (e.g., the tensor 213) by stacking these values. Additionally or alternatively, any suitable method for generating the tensor 213 can be executed. Once the tensor 213 has been generated, the process 700 advances to block 708.

At block 708, the neural network 214 classifies the HPI 108. Additional detail in the execution of block 708 is provided below in conjunction with FIG. 8. Once the HPI classification 110 has been determined, the process 700 advances to block 710. At block 710, the medical system interface 220 modifies a medical support system (e.g., the medical support system 106) based on the HPI 110 classified. In some examples, the medical support interface 220 also modifies the medical support system 106 with unclassified HPI 108. In some examples, the medical system interface 220 may trigger an action from the medical support system 106. For example, the medical system interface 220 can trigger, facilitate and/or otherwise cause the medical support system 106 to schedule a lab test (e.g., bloodwork, etc.) and/or a medical procedure. In some examples, the medical system interface 220 can trigger, facilitate, and/or otherwise cause the medical support system 106 to generate a bill and/or an insurance claim. Additionally or alternatively, the medical system interface 220 can trigger, facilitate, and/or otherwise cause the medical support system 106 to generate, update or delete a medical record. In some examples, the medical support interface 220 can trigger, facilitate, and/or otherwise cause the medical support system 106 to generate request and/or reminder for an appointment. In some examples, the medical support interface 220 can trigger, facilitate, and/or otherwise cause the medical support system 106 to issue a reminder to the data source 102 to retake the HPI 108. Additionally or alternatively, the medical support system 106 can trigger facilitate, and/or otherwise cause any other suitable action from the medical support system 106 such as schedule an imaging exam, trigger a reminder for clinician follow-up, configure an imaging workstation and/or other clinician computing device for patient data analysis, etc.

At block 712, process control decides whether the neural network 214 needs to be retrained. In some examples, the retraining decision is based on whether as many or more than a threshold of incorrectly labeled HPIs have been accrued. Alternatively, the decision to retrain the neural network 214 can instead base on a time interval (e.g., monthly, yearly, etc.). Additionally or alternatively, the neural network 214 can be retrained based on a user, application, and/or system trigger (e.g., by the by an administrator of the medical support system 106 by a billing system, etc.). If the neural network 214 is to be retrained, the process 700 advances to block 714. If the neural network 214 is not to be retrained, the process 700 ends. At block 714, the model trainer 224 retrains the neural network 214. Additional detail in the execution of block 714 is provided below in conjunction with FIG. 10.

Figure 8:
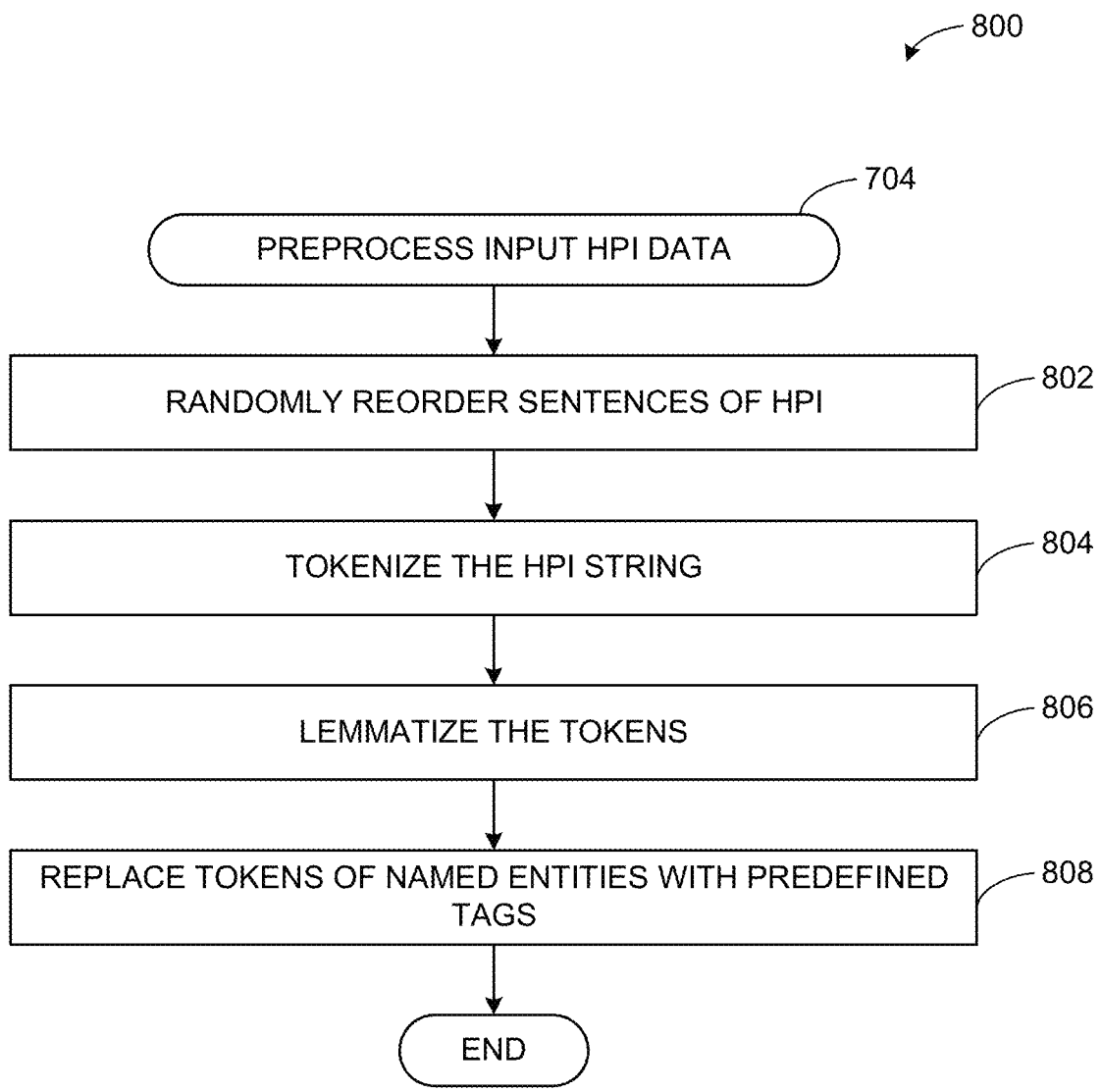
FIG. 8 is a flowchart representative of machine readable instructions which can be executed to preprocess input HPI data.

The subprocess 800 of FIG. 8 depicts the execution of block 704 of FIG. 7 in greater detail. Subprocess 800 begins at block 802. At block 802, the sentence reorderer 209 randomly reorders each sentence of the HPI 108. For example, the sentence reorderer 209 parses the input HPI 108 to determine sentences (e.g., by punctuation, capital, or any other suitable method to parse a text string into sentences). In this example, the sentence reorderer 209 then randomly shuffles the ordering of the sentences in the HPI 108. In some examples, reshuffling the HPI 108 prevents the neural network 214 from being trained to classify the HPI 108 on the ordering of elements instead of their presence. Alternatively, any other suitable method can be used to randomly reorder the sentences of the HPI 108. In some examples, the sentence reorderer 209 can then concatenate the parsed sentences into a single text string. The subprocess 800 then advances to block 804.

At block 804, the tokenizer 206 tokenizes the HPI 108. For example, the tokenizer 206 can parse the HPI 108 into individual tokens. In some examples, the tokenizer 206 tokenizes the HPI 108 by identifying a "space" or " " delimiter. In other examples, the tokenizer 206 can tokenizer the HPI 108 by identifying other punctuation, sentence/phrase structure, related terms, etc. In some examples, the tokenizer 206 can have special-case rules which allow for certain types of phrases (e.g., dates, Names, medical terms, etc.) to be tokenized together. Once the HPI 108 has been tokenized, the subprocess 800 advances to block 806.

At block 806, the lemmatizer 208 lemmatizes the tokens of the HPI 108. For example, the lemmatizer scans each token and replaces each token with a lemma associated with that token. In some examples, the lemmatizer 208 can leverage a database of words and their associated lemmas. In some examples, the lemmatizer 208 utilizes a simple or a neural network to determine a context of a token. In this example, the context of a token can be used to determine its proper lemma (e.g., the word drawer has multiple lemmas).

Alternatively, any suitable method can be used to replace tokens with their lemmas. The subprocess 800 then advances to block 808.

At block 808, the named entity recognizer 210 replaces the tokens of named entities with predefined tags. For example, the named entity recognizer 210 parses the lemmatized tokens for any named entities and replaces each named entity with a tag from a database. In some examples, named entities, such as places, people and dates, are replaced with a predetermined tag. In some examples, the named entity recognizer 210 also replaces misspellings and other tokens that the named entity recognizer 210 does not recognize with a separate tag indicating the word is out of vocabulary (e.g., "OVV"). Once the HPI 108 has been preprocessed into the preprocessed HPI 211, the subprocess 800 returns to process 700.

Figure 9:
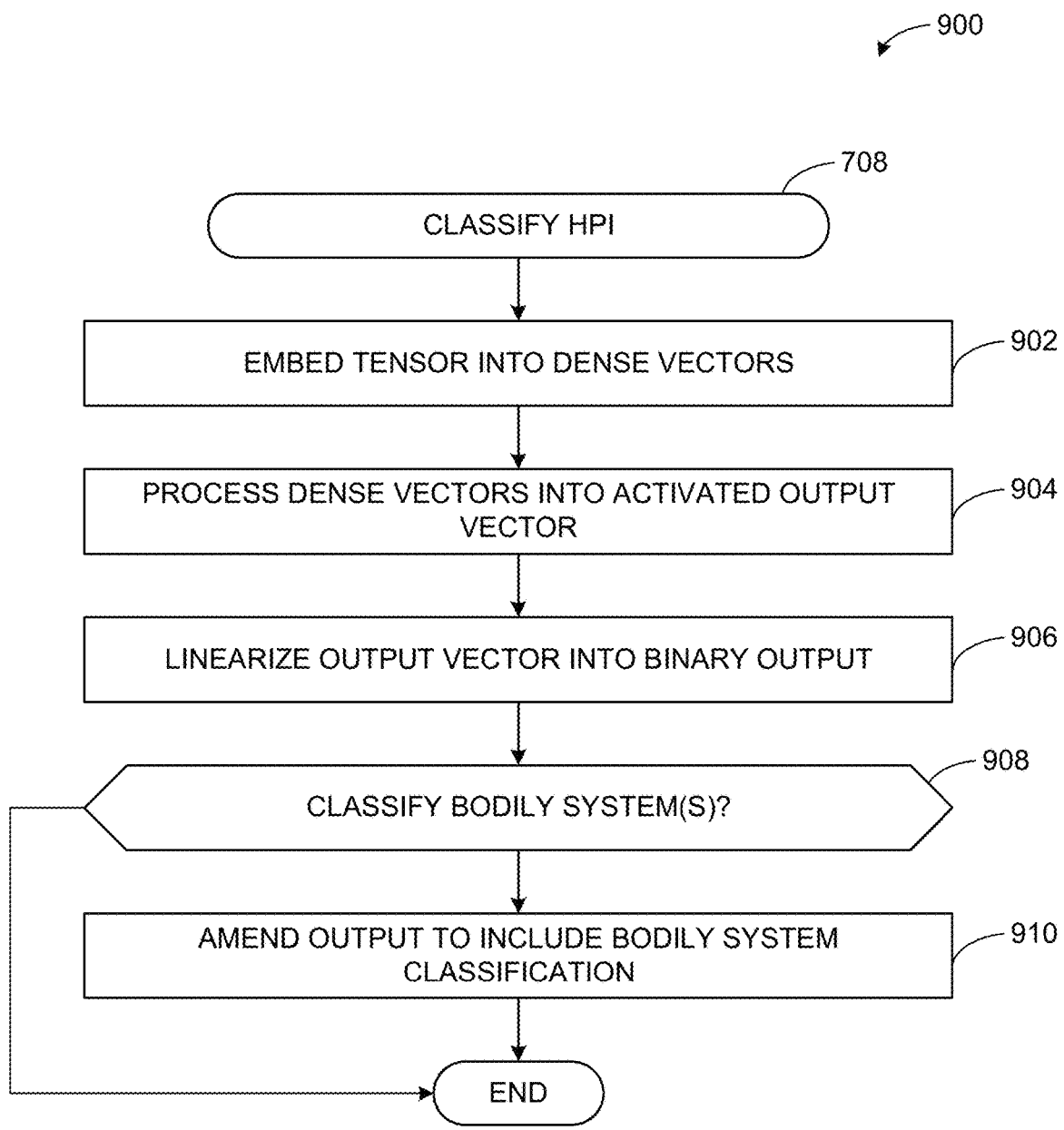
FIG. 9 is a flowchart representative of machine readable instructions which can be executed to classify the preprocessed HPI data.

The subprocess 900 of FIG. 9 depicts the execution of block 708 of FIG. 7 in greater detail. Subprocess 900 begins at block 902. At block 902, the embedding layer 216 embeds the tensor 213 into dense vectors. For example, the embedding layer 216 converts each element (e.g., vector or scalar) of the tensor 213 into a dense vector. In some examples, the length (e.g., the number of dimensions) of the dense vector is a fixed and predetermined quantity. In some examples, the particular mathematical process to embed the tensor 213 into dense vectors is optimized and/or otherwise improved during the training of the neural network 214. Once the tensor 213 has been embedded into dense vectors, the subprocess 900 advances to block 904.

At block 904, the LSTM layer 218 processes the dense vectors into an activated output vector. In some examples, the LSTM layer 218 uses a soft-sign activation function. In other examples, the LSTM layer 218 uses another suitable activation function (e.g., a hyperbolic tangent function, etc.). In some examples, the particular mathematical process to generate the activated output vector is optimized and/or otherwise improved during the training of the neural network 214. Once the output vector has been generated, the subprocess 900 advances to block 906.

At block 906, the fully connected layer 220 linearizes the output vector in a binary output. For example, the fully connected layer 220 uses a sigmoid activation function and/or matrix multiplication to convert the output vector in binary output. In some examples, the fully connected layer 220 linearizes the output vector and then rounds the output into a binary output (e.g., "0" or "1"). In some examples, the binary output is the HPI classification 110 (e.g., "1" corresponds to brief and "0" corresponds to extended). Alternatively, the full connected layer can have multiple outputs which include the HPI classification 110. Once the HPI classification 110 has been generated, the subprocess 900 advances to block 908.

At block 908, process control decides whether the fully connected layer 220 is to classify the body system(s) described in the input HPI. If the fully connected layer 220 is classify the bodily system(s) described in the input HPI, the subprocess 900 advances to block 910. If the fully connected layer 220 is not to be classified, the subprocess ends and returns to process 700. At block 910, the fully connected layer 220 amends the output to include a bodily system classification. For example, the fully connected layer 220 can include a binary output for each notable bodily system (e.g., circulatory, endocrine, lymphatic, etc.). In other examples, the fully connected layer 220 can include a probability that the input HPI pertains to a particular bodily system. Once the output has been amended to include a bodily system classification, the subprocess 900 ends and returns to process 700.

Figure 10:
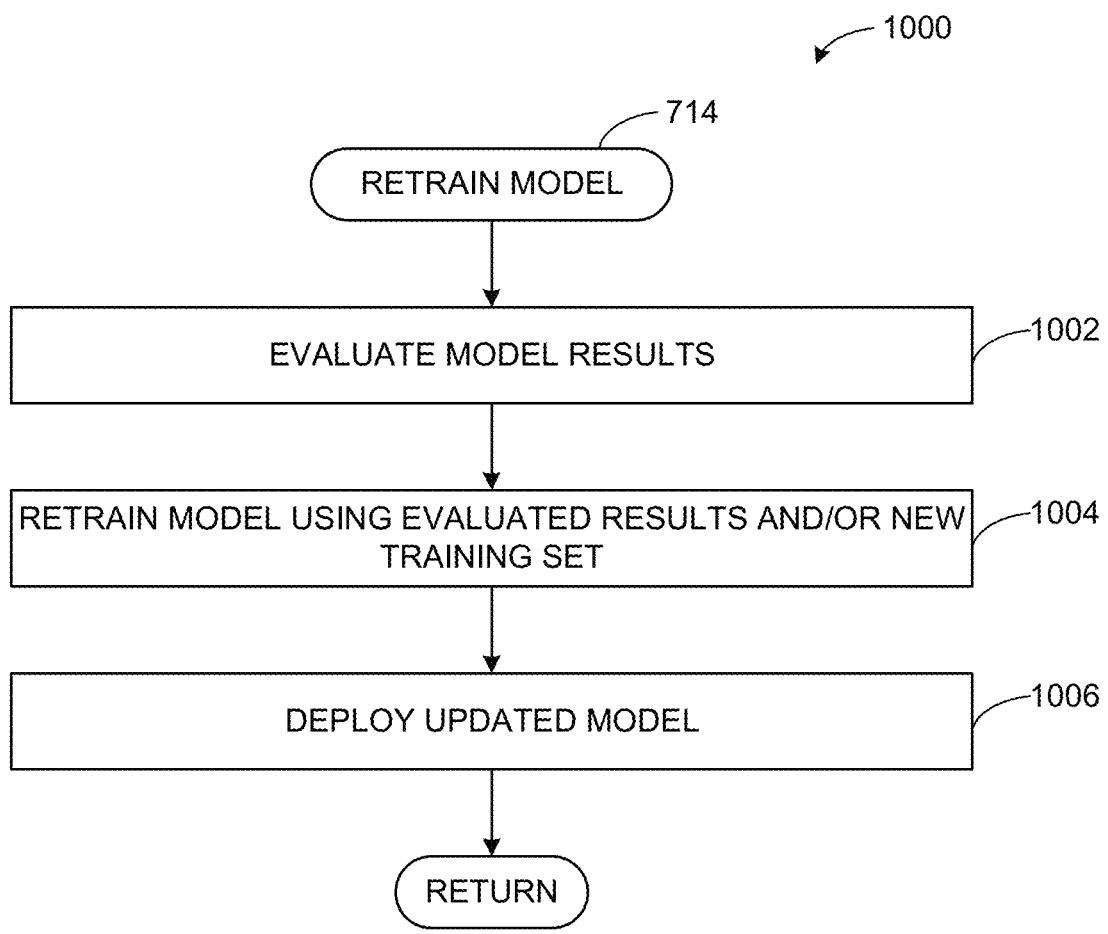
FIG. 10 is a flowchart representative of machine readable instructions which can be executed to retrain the HPI model.

The subprocess 1000 of FIG. 10 depicts the execution of block 714 of FIG. 7 in greater detail. At block 1002, the model evaluator 222 evaluates model results (e.g., the output of the neural network 214). For example, the model evaluator 222 can randomly sample the model results (e.g., the HPI classifications 110) and submit them to be independently evaluated. In this example, the model evaluator 222 can compiles feedback provided by healthcare professionals and/or third party entities (e.g., an insurance company, the CMS, etc.) on the sampled model results. In some examples, if the independently evaluated model results do not satisfy an accuracy threshold, the model evaluator 222 can create a new set of pre-classified training and validation HPIs. In other examples, the model evaluator 222 can create a new set of training and validation HPI regardless of the accuracy the model results. In some examples, the model evaluator 222 continues to collect feedback until a threshold of feedback has been received. In some examples, the model evaluator 222 can evaluate the model periodically (e.g., quarterly, etc.). Once a suitable level of feedback has been collected, the subprocess 1000 advances to block 1004.

At block 1004, the model trainer 224 retrains the model using the evaluated results and/or new training set. For example, the model trainer 224 can divide the collected feedback and/or new training set into a training set of HPIs and a validation set of HPIs. In some examples, the model trainer 224 can add pre-classified HPIs from previous sets into the training set and/or validation set. In some examples, the model trainer 224, starting with the current neural network 214, begins using the training set to iteratively change the strength of connections between nodes in each layer (e.g., the embedding layer 216, the LSTM layer 218 and/or fully connected layer 220, etc.) until a deserved accuracy of classification is achieved. In this example, after the deserved accuracy is achieved, the validation set of HPIs is used to verify the fidelity of the newly trainer neural network. In some examples, the model trainer 224 may change the activation functions used by neural network 214 (e.g., change the activation function of the LSTM layer 218 to a Tan h activation function, etc.). Once the newly trained neural network has been deployed, the subprocess 1000 advances to block 1006.

At block 1006, the model deployer 226 deploys the newly trained neural network. For example, the model deployer 226 can replace the currently used neural network 214 with the newly trained neural network model/construct. In some examples, the model deployer 226 makes the connections between nodes of the neural network rigid so they do not change when deployed in the HPI classifier 104. Once the neural network has been replaced, the subprocess 1000 ends and returns to the process 700.

Figure 11:
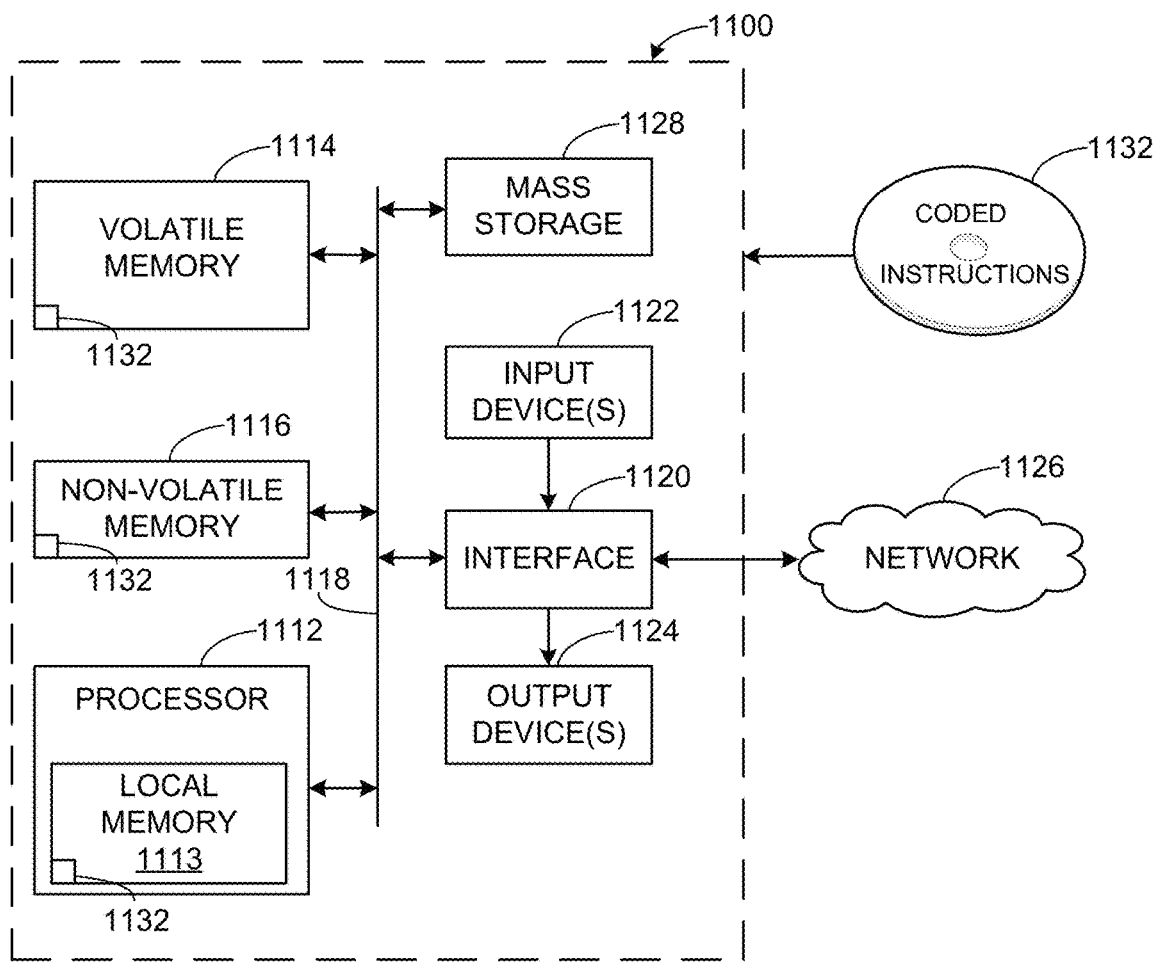
FIG. 11 is a block diagram of an example processing platform structured to execute the instructions of FIGS. 7-10 to implement the systems and methods described herein including the HPI classifier and/or other components of FIG. 2.

FIG. 11 is a block diagram of an example processor platform 1100 structured to execute the instructions of FIGS. 7-10 to implement the HPI classifier 104 of FIG. 2. The processor platform 1100 can be, for example, a server, a personal computer, a workstation, a self-learning machine (e.g., a neural network), a mobile device (e.g., a cell phone, a smart phone, a tablet such as an iPad™), a personal digital assistant (PDA), an Internet appliance, a DVD player, a CD player, a digital video recorder, a Blu-ray player, a gaming console, a personal video recorder, a set top box, a headset or other wearable device, or any other type of computing device.

The processor platform 1100 of the illustrated example includes a processor 1112. The processor 1112 of the illustrated example is hardware. For example, the processor 1112 can be implemented by one or more integrated circuits, logic circuits, microprocessors, GPUs, DSPs, or controllers from any desired family or manufacturer. The hardware processor may be a semiconductor based (e.g., silicon based) device. In this example, the processor 1112 implements the example preprocessor 202, the example natural language processor 204, the example tokenizer 206, the example lemmatizer 208, the example sentence reorderer 209, the example named entity recognizer 210, the example tensor generator 212, the example neural network 214, the example embedding layer 216, the example LSTM layer 218, and the example fully connected layer 220.

The processor 1112 of the illustrated example includes a local memory 1113 (e.g., a cache). The processor 1112 of the illustrated example is in communication with a main memory including a volatile memory 1114 and a non-volatile memory 1116 via a bus 1118. The volatile memory 1114 may be implemented by Synchronous Dynamic Random Access Memory (SDRAM), Dynamic Random Access Memory (DRAM), RAMBUS® Dynamic Random Access Memory (RDRAM®), and/or any other type of random access memory device. The non-volatile memory 1116 may be implemented by flash memory and/or any other desired type of memory device. Access to the main memory 1114, 1116 is controlled by a memory controller.

The processor platform 1100 of the illustrated example also includes an interface circuit 1120. The interface circuit 1120 may be implemented by any type of interface standard, such as an Ethernet interface, a universal serial bus (USB), a Bluetooth® interface, a near field communication (NFC) interface, and/or a PCI express interface.

In the illustrated example, one or more input devices 1122 are connected to the interface circuit 1120. The input device(s) 1122 permit(s) a user to enter data and/or commands into the processor 1112. The input device(s) can be implemented by, for example, an audio sensor, a microphone, a camera (still or video), a keyboard, a button, a mouse, a touchscreen, a track-pad, a trackball, an isopoint device, and/or a voice recognition system.

One or more output devices 1124 are also connected to the interface circuit 1120 of the illustrated example. The output devices 1124 can be implemented, for example, by display devices (e.g., a light emitting diode (LED), an organic light emitting diode (OLED), a liquid crystal display (LCD), a cathode ray tube display (CRT), an in-place switching (IPS) display, a touchscreen, etc.), a tactile output device, a printer, and/or speaker. The interface circuit 1120 of the illustrated example, thus, typically includes a graphics driver card, a graphics driver chip, and/or a graphics driver processor.

The interface circuit 1120 of the illustrated example also includes a communication device such as a transmitter, a receiver, a transceiver, a modem, a residential gateway, a wireless access point, and/or a network interface to facilitate exchange of data with external machines (e.g., computing devices of any kind) via a network 1126. The communication can be via, for example, an Ethernet connection, a digital subscriber line (DSL) connection, a telephone line connection, a coaxial cable system, a satellite system, a line-of-site wireless system, a cellular telephone system, etc.

The processor platform 1100 of the illustrated example also includes one or more mass storage devices 1128 for storing software and/or data. Examples of such mass storage devices 1128 include floppy disk drives, hard drive disks, compact disk drives, Blu-ray disk drives, redundant array of independent disks (RAID) systems, and digital versatile disk (DVD) drives.

The machine executable instructions 1132 of FIGS. 7-10 may be stored in the mass storage device 1128, in the volatile memory 1114, in the non-volatile memory 1116, and/or on a removable non-transitory computer readable storage medium such as a CD or DVD.

From the foregoing, it will be appreciated that example methods, apparatus and articles of manufacture have been disclosed that classify medical data using an artificial intelligence. The disclosed examples offer several advantages over manually classified HPI. The disclosed examples improve medical data processing for computer-aided diagnosis, billing, treatment approval, and other patient safety and patient care. The disclosed examples improve operation of healthcare data processors by correctly and efficiently processing a variety of available information and generating a consistent, accurate result. The disclosed examples decrease the probability of denied reimbursement due to incorrect HPI classification.

On a broader scale, automatic HPI classification can be part of Clinical Documentation Improvement (CDI). Successful CDI programs facilitate the accurate representation of a patient's clinical status that translates into coded data. Coded data is then translated into quality reporting, physician report cards, reimbursement, public health data, patient care plan, and disease tracking and trending.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent.

What is claimed:

1. An apparatus comprising:
a processor to execute instructions to implement at least:
   a history of past illness (HPI) receiver to receive an HPI formatted as a string, the string including one or more words, the words organized in an order of sentences;
   a natural language processor to tokenize the one or more words into tokens based on a context associated with at least one of the one or more words;
   a tensor generator to convert the tokens into hashes, each of the hashes forming a dimension of a tensor based on the context;
   a neural network to:
      embed each of the hashes into vectors;
      process the vectors to classify the HPI as extended or brief based on a similarity to a set of classified HPIs; and
      output a classification for the HPI; and
   a medical system interface to modify a medical support system with the HPI and the classification and to trigger an action with respect to the medical support system based on the classification.

2. The apparatus of claim 1, wherein the natural language processor is further to:
randomize the order of the sentences of the HPI;
lemmatize the words into lemmas; and
replace the tokens of named entities with predefined tags associated with each type of named entities.

3. The apparatus of claim 2, where the types of the named entities include at least one of dates, locations, times, quantities, people or out-of-vocabulary words.

4. The apparatus of claim 1, wherein the neural network is a three-layer recurrent neural network including an embedding layer, a long short-term memory (LSTM) layer and a fully connected layer.

5. The apparatus of claim 4, wherein the fully connected layer generates a binary output using a sigmoid activation function, the binary output indicating the classification of the HPI.

6. The apparatus of claim 1, wherein each HPI of the set of classified HPIs is classified based on an identification of four or more HPI criteria, the HPI criteria including (2) quality of problem, (3) severity of problem, (4) duration of problem, (5) context of problem, (6) modifying factors, and (7) associated signs and symptoms.

7. The apparatus of claim 1, wherein the hashes are integers based on a sparse vector generated via one hot encoding.

8. The apparatus of claim 1, wherein the neural network is to further identify a bodily system described in the HPI.

9. The apparatus of claim 1, wherein the medical support system includes at least one of an electronic medical record, medical billing system or computer-aided diagnosis system.

10. A method comprising:
receiving an HPI formatted as a string, the string including one or more words, the words organized in an order of sentences;
tokenizing the one or more words into tokens based on a context associated with at least one of the one or more words;
converting the tokens into hashes, each of the hashes forming a dimension of a tensor based on the context;
embedding each of the hashes into vectors;
processing the vectors to classify the HPI as extended or brief based on a similarity to a set of classified HPIs;
outputting a classification for the HPI; and
modifying a medical support system with the HPI and the classification and to trigger an action with respect to the medical support system based on the classification.

11. The method of claim 10 further including:
randomizing the order of the sentences of the HPI;
lemmatizing the words into lemmas; and
replacing the tokens of named entities with predefined tags associated with each type of the named entities.

12. The method of claim 11, where the types of the named entities include at least one of dates, locations, times, quantities, people or out-of-vocabulary words.

13. The method of claim 10, further including generating a binary output using a sigmoid activation function, the binary output indicating the classification of the HPI.

14. The method of claim 10, further including identifying a bodily system described in the HPI.

15. The method of claim 10, wherein each HPI of the set of classified HPIs is classified based on an identification of four or more HPI criteria, the HPI criteria including (2) quality of problem, (3) severity of problem, (4) duration of problem, (5) context of problem, (6) modifying factors, and (7) associated signs and symptoms.

16. A tangible machine readable medium comprising instructions, which when executed, cause a processor to at least:
receive an HPI formatted as a string, the string including one or more words, the words organized in an order of sentences;
tokenize the one or more words into tokens based on a context associated with at least one of the one or more words;
convert the tokens into hashes, each of the hashes forming a dimension of a tensor based on the context;
embed each of the hashes into vectors;
process the vectors to classify the HPI as extended or brief based on a similarity to a set of classified HPIs;
output a classification for the HPI; and
modify a medical support system with the HPI and the classification and to trigger an action with respect to the medical support system based on the classification.

17. The tangible machine readable medium of claim 16, further including instructions, which when executed, cause the processor to:
randomize the order of the sentences of the HPI;
lemmatize the words into lemmas; and
replace the tokens of named entities with predefined tags associated with each type of the named entities.

18. The tangible machine readable medium of claim 17, wherein the types of the named entities include at least one of dates, locations, times, quantities, people or out-of-vocabulary words.

19. The tangible machine readable medium of claim 16, further including instructions, which when executed, cause the processor to generate a binary output using a sigmoid activation function, the binary output indicating the classification of the HPI.

20. The tangible machine readable medium of claim 16, further including instructions, which when executed, cause the processor to identify a bodily system described in the HPI.

* * * * *

UNITED STATES PATENT AND TRADEMARK OFFICE
CERTIFICATE OF CORRECTION

PATENT NO. : 10,784,000 B2
APPLICATION NO. : 16/136984
DATED : September 22, 2020
INVENTOR(S) : Eric Wu et al.

Page 1 of 1

It is certified that error appears in the above-identified patent and that said Letters Patent is hereby corrected as shown below:

In the Drawings

On sheet 7 of 11, in Figure 7, reference numeral 710, Line 2, delete "CLASSIFED" and insert -- CLASSIFIED --, therefor.

In the Specification

In Column 4, Line 43, delete "(supracerivcal)." and insert -- (supracervical). --, therefor.

In Column 4, Line 63, delete "fo" and insert -- of --, therefor.

In Column 4, Line 64, delete "no" and insert -- not --, therefor.

In Column 5, Line 37, delete "all" and insert -- All --, therefor.

In Column 18, Line 56, delete "Names," and insert -- names, --, therefor.

In Column 19, Line 15, delete ""OVV")." and insert -- "OOV"). --, therefor.

Signed and Sealed this
Tenth Day of November, 2020

Andrei Iancu
*Director of the United States Patent and Trademark Office*